(12) United States Patent
Dubensky, Jr. et al.

(10) Patent No.: US 7,744,900 B2
(45) Date of Patent: Jun. 29, 2010

(54) ENHANCEMENT OF THE IMMUNE RESPONSE FOR VACCINE AND GENE THERAPY APPLICATIONS

(75) Inventors: Thomas W Dubensky, Jr., Piedmont, CA (US); John M Polo, Hayward, CA (US); Barbara A Belli, San Diego, CA (US); Silvia Perri, Castro Valley, CA (US); Timothy C Fong, Moraga, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 0 days.

(21) Appl. No.: 12/111,305

(22) Filed: Apr. 29, 2008

(65) Prior Publication Data

US 2008/0292655 A1 Nov. 27, 2008

Related U.S. Application Data

(62) Division of application No. 09/546,201, filed on Apr. 10, 2000, now abandoned.

(60) Provisional application No. 60/128,409, filed on Apr. 8, 1999.

(51) Int. Cl.
| | |
|---|---|
| A61K 39/12 | (2006.01) |
| C12P 21/02 | (2006.01) |
| C12P 15/00 | (2006.01) |
| C07H 21/04 | (2006.01) |

(52) U.S. Cl. .............. 424/199.1; 435/320.1; 435/69.51; 536/23.72

(58) Field of Classification Search ........................ None
See application file for complete search history.

(56) References Cited

U.S. PATENT DOCUMENTS

| | | | |
|---|---|---|---|
| 5,736,388 A | 4/1998 | Chada | |
| 5,935,937 A | 8/1999 | Smith | |
| 6,015,686 A | 1/2000 | Dubensky | |

FOREIGN PATENT DOCUMENTS

WO    WO 90/14090    11/1990

OTHER PUBLICATIONS

Levandowski and Horohov. Rhinovirus induces natural killer-like cytotoxic cells and interferon alpha in mononuclear leukocytes. (1991) J. Medical Virology. 35: 116-120.*

Mertens, et al., "Versatile, Multi-Featured Plasmids for High-Level Expression of Heterologous Genes in *Escherichia coli*: Overproduction of Human and Murine Cytokines" *Gene* 164;9-15, 1995.
Gessani et al., "Activators of Protein Kinase C Enhance Accumulation of Interferon-β mRNA in Murine Cell Lines" *J. Interferon Research* 9:543-550, 1989.
Mory et al., "Production of Two Human 2', 5'-Oligoadenylate Synthetase Enzymes in *Escherichia coli*" *J. Interferon Research* 9:295-304, 1989.
Ivanov et al., "Expression of Human Alpha I Interferon Genes in Vectors Containing Tandemly Located Promoters Recognized by Two Different RNA Polymerases (*Escherichia coli* and T7)" *FEMS Microbiology Letters* 108:231-236, 1993.
Page, "Expression of Amplified Human Beta Interferon Genes Using Heavy Metal Induction in Chinese Hamster Ovary Cells" *Gene* 37:139-144, 1985.
Bertrand et al., "The Expression Cassette Determines the Functional Activity of Ribozymes in Mammalian Cells by Controlling Their Intracellular Localization" *RNA* 3:75-88, 1997.
Wakita et al., "Antiviral Effects of Antisense RNA on Hepatitis C Virus RNA Translation and Expression" *J. Medical Virology* 57:217-222, 1999.
Polo et al., "Stable Alphavirus Packaging Cell Lines for Sindbis Virus- and Semliki Forest Virus-Derived Vectors" *Proc. Natl. Acad. Sci. USA* 96:4598-4603, Apr. 1999.
U.S. Appl. No. 09/546,201, filed Feb. 29, 2008, Decision on Appeal.
Leitner et al., "Enhancement of tumor-specific immune response with plasmid DNA replicon vectors," *Cancer Res. 60*, 51-55, Jan. 1, 2000.
Polo et al., "DNA vaccines with a kick," *Nature Biotechnology 16*, 517-18, 1998.
Berglund et al., "Enhancing immune responses using suicidal DNA vaccines," *Nature Biotechnology 16*, 562-65, 1998.
Cella et al., *J. Exp. Med.* 189, 821-29, 1999.

* cited by examiner

*Primary Examiner*—Zachariah Lucas
*Assistant Examiner*—Michelle Horning
(74) *Attorney, Agent, or Firm*—Helen Lee; Lisa M. Hemmendinger; Robert Gorman

(57) ABSTRACT

Expression cassettes are provided comprising a promoter operably linked to a nucleic acid molecule which, when transcribed in vivo, forms double-stranded RNA that induces the production of interferon. Expression cassettes also are provided comprising a promoter operably linked to a ribozyme or antisense nucleic acid molecule which, when transcribed in vivo, forms a ribozyme or antisense RNA molecule that stimulates an immune response. In addition, expression cassettes are provided comprising a promoter operably linked to a ribozyme or antisense nucleic acid molecule which, when transcribed in vivo, stimulates apoptosis. Finally, gene delivery vectors are provided which contain such expression cassettes, host cells containing the gene delivery vectors, and methods of utilizing the expression cassettes, gene delivery vectors, and host cells.

15 Claims, 6 Drawing Sheets

Plasmid vector with dsRNA and antigen cassettes

Pro-apoptotic vectors with antigen cassettes

OR

IL10

```
  1 AAACCACAAGACAGACTTGCAAAAGAAGGCATGCACAGCTCAGCACTGCTCTGTTGCCTGGTCCTCCTGACT
    TTTGGTGTTCTGTCTGAACGTTTTCTTCCGTACGTGTCGAGTCGTGACGAGACAACGGACCAGGAGGACTGA
 73 GGGGTGAGGGCCAGCCCAGGCCAGGGCACCCAGTCTGAGAACAGCTGCACCCACTTCCCAGGCAACCTGCCTA
    CCCCACTCCCGGTCGGGTCCGGTCCCGTGGGTCAGACTCTTGTCGACGTGGGTGAAGGGTCCGTTGGACGGAT
146 ACATGCTTCGAGATCTCCGAGATGCCTTCAGCAGAGTGAAGACTTTCTTTCAAATGAAGGATCAGCTGGACAAC
    TGTACGAAGCTCTAGAGGCTCTACGGAAGTCGTCTCACTTCTGAAAGAAAGTTTACTTCCTAGTCGACCTGTTG
220 TTGTTGTTAAAGGAGTCCTTGCTGGAGGACTTTAAGGGTTACCTGGGTTGCCAAGCCTTGTCTGAGATG
    AACAACAATTTCCTCAGGAACGACCTCCTGAAATTCCCAATGGACCCAACGGTTCGGAACAGACTCTAC
```

COX2

```
  1 GTCCAGGAACTCCTCAGCAGCGCCTCCTTCAGCTCCACAGCCAGACGCCCTCAGACAGCAAAGCCTACCCCCG
    CAGGTCCTTGAGGAGTCGTCGCGGAGGAAGTCGAGGTGTCGGTCTGCGGGAGTCTGTCGTTTCGGATGGGGGC
 74 CGCCGCGCCCTGCCCGCCGCTGCGATGCTCGCCCGCGCCCTGCTGCTGTGCGCGGTCCTGGCGCTCAGCCATACA
    GCGGCGCGGGACGGGCGGCGACGCTACGAGCGGGCGCGGGACGACGACACGCGCCAGGACCGCGAGTCGGTATGT
149 GCAAATCCTTGCTGTTCCCACCCATGTCAAAACCGAGGTGTATGTATGAGTGTGGGATTTGACCAGTATAAGTGCG
    CGTTTAGGAACGACAAGGGTGGGTACAGTTTTGGCTCCACATACATACTCACACCCTAAACTGGTCATATTCACGC
225 ATTGTACCCGGACAGGATTCTATGGAGAAAACTGCTCAACACCGGAATTTTTGACAAGAATAAAATTATTTC
    TAACATGGGCCTGTCCTAAGATACCTCTTTTGACGAGTTGTGGCCTTAAAAACTGTTCTTATTTTAATAAAG
```

YY1

```
  1 CGCCGAGACGAGCAGCGGCCGAGCGAGCGCGGGCGCGGGCGCACCGAGGCGAGGGAGGCGGGGAAGCCCCGCCGCCG
    GCGGCTCTGCTCGTCGCCGGCTCGCTCGCGCCCGCGCCCCGCGTGGCTCCGCTCCCTCCGCCCCTTCGGGGCGGCGGC
 78 CCGCCCCGCCCGCCCCTTCCCCCGCCGCCCGCCCCCTCTCCCCCCGCCCGCTCGCCGCCTTCCTCCCTCTGCCTT
    GGCGGGGCGGGCGGGGAAGGGGGCGGCGGGCGGGGGAGAGGGGGCGGGCGAGCGGCGGAAGGAGGGAGACGGAA
153 CCTTCCCCACGGCCGGCCGCCTCCTCGCCCGCCCGCCCGCAGCCGAGGAGCCGAGGCCGCCGCGGCCGTGGCGGC
    GGAAGGGGTGCCGGCCGGCGGAGGAGCGGGCGGGCGGGCGTCGGCTCCTCGGCTCCGGCGGCGCCGGCACCGCCG
228 GGAGCCCTCAGCCATGGCCTCGGGCCGACACCCTCTACATCGCCACGGACGGCTCGGAGATGCCGGCCGAGATCGTGG
    CCTCGGGAGTCGGTACCGGAGCCCGCTGTGGGAGATGTAGCGGTGCCTGCCGAGCCTCTACGGCCGGCTCTAGCACC
305 AGCTGCACGAGATCGAGGTGGAGACCATCCCGGTGGAGACCATCGAGACCACAGTGGTGGGCGAGGAGGAGG
    TCGACGTGCTCTAGCTCCACCTCTGGTAGGGCCACCTCTGGTAGCTCTGGTGTCACCACCCGCTCCTCCTCC
```

IRF2

```
  1 AACTGACGGGCTTTCATTTCCATTTCACACACCCTAGCAACACTTATACCTTGCGGAATTGTATTGGTAGC
    TTGACTGCCCGAAAGTAAAGGTAAAGTGTGTGGGATCGTTGTGAATATGGAACGCCTTAACATAACCATCG
 72 GTGAAAAAAGCACACTGAGAGGGCACCATGCCGGTGGAAAGGATGCGCATGCGCCCGTGGCTGGAGGAGCAGAT
    CACTTTTTTCGTGTGACTCTCCCGTGGTACGGCCACCTTTCCTACGCGTACGCGGGCACCGACCTCCTCGTCTA
146 AAACTCCAACACGATCCCGGGGCTCAAGTGGCTTAACAAGGAAAAGAAGATTTTTCAGATCCCCTGGATGCAT
    TTTGAGGTTGTGCTAGGGCCCCGAGTTCACCGAATTGTTCCTTTTCTTCTAAAAAGTCTAGGGGACCTACGTA
219 GCGGCTAGACATGGGTGGGATGTGGAAAAAGATGCACCACTCTTTAGAAACCGGGCAATCCATACAGGAA
    CGCCGATCTGTACCCACCCTACACCTTTTTCTACGTGGTGAGAAATCTTTGGCCCGTTAGGTATGTCCTT
289 AGCATCAACCAGGAGTAGATAAACCTGATCCCAAAACATGGAAGGCGAATTTCAGATGCGCCATGAATTCCTT
    TCGTAGTTGGTCCTCATCTATTTGGACTAGGGTTTTGTACCTTCCGCTTAAAGTCTACGCGGTACTTAAGGAA
362 GCCTGATATTGAAGAAGTCAAGGATAAAAGCATAAAGAAAGGAAATAATGCCTTCAGGGTCTACCGAATGCTG
    CGGACTATAACTTCTTCAGTTCCTATTTTCGTATTTCTTTCCTTTTATTACGGAAGTCCCAGATGGCTTACGAC
```

*Fig. 6*

SEQUENCE LISTING

```
<160> NUMBER OF SEQ ID NOS: 70

<210> SEQ ID NO 1
<211> LENGTH: 434
<212> TYPE: DNA
<213> ORGANISM: Artificial
<220> FEATURE:
<223> OTHER INFORMATION: IRF2
<220> FEATURE:
<221> NAME/KEY: misc_feature
<222> LOCATION: (11)..(13)
<223> OTHER INFORMATION: target sequence for hammerhead ribozyme
<220> FEATURE:
<221> NAME/KEY: misc_feature
<222> LOCATION: (43)..(45)
<223> OTHER INFORMATION: target sequence for hammerhead ribozyme
<220> FEATURE:
<221> NAME/KEY: misc_feature
<222> LOCATION: (50)..(52)
<223> OTHER INFORMATION: target sequence for hammerhead ribozyme
<220> FEATURE:
<221> NAME/KEY: misc_feature
<222> LOCATION: (50)..(89)
<223> OTHER INFORMATION: complementary sequence for the hammerhead
      ribozyme
<220> FEATURE:
<221> NAME/KEY: misc_feature
<222> LOCATION: (61)..(63)
<223> OTHER INFORMATION: target sequence for hammerhead ribozyme
<220> FEATURE:
<221> NAME/KEY: misc_feature
<222> LOCATION: (67)..(69)
<223> OTHER INFORMATION: target sequence for a chosen ribozyme
<220> FEATURE:
<221> NAME/KEY: misc_feature
<222> LOCATION: (99)..(101)
<223> OTHER INFORMATION: starting Met
<220> FEATURE:
<221> NAME/KEY: misc_feature
<222> LOCATION: (177)..(179)
<223> OTHER INFORMATION: target sequence for hammerhead ribozyme
<220> FEATURE:
<221> NAME/KEY: misc_feature
<222> LOCATION: (303)..(305)
<223> OTHER INFORMATION: target sequence for hammerhead ribozyme
<220> FEATURE:
<221> NAME/KEY: misc_feature
<222> LOCATION: (378)..(380)
<223> OTHER INFORMATION: target sequence for hammerhead ribozyme
<220> FEATURE:
<221> NAME/KEY: misc_feature
```

```
<222> LOCATION: (418)..(418)
<223> OTHER INFORMATION: target sequences for both hammerhead and
      hairpin ribozymes
<220> FEATURE:
<221> NAME/KEY: misc_feature
<222> LOCATION: (420)..(422)
<223> OTHER INFORMATION: target sequences for both hammerhead and
      hairpin ribozymes

<400> SEQUENCE: 1
aactgacggg ctttcatttc catttcacac accctagcaa cacttatacc ttgcggaatt      60
gtattggtag cgtgaaaaaa gcacactgag agggcaccat gccggtggaa aggatgcgca    120
tgcgcccgtg gctggaggag cagataaact ccaacacgat cccggggctc aagtggctta    180
acaaggaaaa gaagattttt cagatcccct ggatgcatgc ggctagacat gggtgggatg    240 tggaaaaga tgcaccactc tttagaaacc gggcaatcca tacaggaaag catcaaccag     300
gagtagataa acctgatccc aaaacatgga aggcgaattt cagatgcgcc atgaattcct    360
tgcctgatat tgaagaagtc aaggataaaa gcataaagaa aggaaataat gccttcaggg    420
tctaccgaat gctg                                                      434

<210> SEQ ID NO 2
<211> LENGTH: 376
<212> TYPE: DNA
<213> ORGANISM: Artificial
<220> FEATURE:
<223> OTHER INFORMATION: YY1
<220> FEATURE:
<221> NAME/KEY: misc_feature
<222> LOCATION: (113)..(115)
<223> OTHER INFORMATION: target sequences for hammerhead ribozyme
<220> FEATURE:
<221> NAME/KEY: misc_feature
<222> LOCATION: (128)..(130)
<223> OTHER INFORMATION: target sequences for hammerhead ribozyme
<220> FEATURE:
<221> NAME/KEY: misc_feature
<222> LOCATION: (140)..(142)
<223> OTHER INFORMATION: target sequences for hammerhead ribozyme
<220> FEATURE:
<221> NAME/KEY: misc_feature
<222> LOCATION: (144)..(146)
<223> OTHER INFORMATION: target sequences for hammerhead ribozyme
<220> FEATURE:
<221> NAME/KEY: misc_feature
<222> LOCATION: (173)..(178)
<223> OTHER INFORMATION: target sequences for hammerhead ribozyme
<220> FEATURE:
<221> NAME/KEY: misc_feature
<222> LOCATION: (228)..(266)
<223> OTHER INFORMATION: complementary sequence for the hammerhead
      ribozyme
<220> FEATURE:
<221> NAME/KEY: misc_feature
<222> LOCATION: (234)..(236)
<223> OTHER INFORMATION: target sequences for hammerhead ribozyme
<220> FEATURE:
<221> NAME/KEY: misc_feature
<222> LOCATION: (241)..(243)
<223> OTHER INFORMATION: starting Met
<220> FEATURE:
<221> NAME/KEY: misc_feature
<222> LOCATION: (246)..(248)
<223> OTHER INFORMATION: target sequences for a chosen ribozyme
<220> FEATURE:
<221> NAME/KEY: misc_feature
<222> LOCATION: (259)..(261)
<223> OTHER INFORMATION: target sequences for hammerhead ribozyme

<400> SEQUENCE: 2
cgccgagacg agcagcggcc gagcgagcgc gggcgcgggc gcaccgaggc gagggaggcg      60
```

```
gggaagcccc gccgccgccg ccccgcccgc cccttccccc gccgcccgcc ccctctcccc    120
ccgcccgctc gccgccttcc tccctctgcc ttccttcccc acggccggcc gcctcctcgc    180
ccgcccgccc gcagccgagg agccgaggcc gccgcggccg tggcggcgga gccctcagcc    240
atggcctcgg gcgacaccct ctacatcgcc acggacggct cggagatgcc ggccgagatc    300
gtggagctgc acgagatcga ggtggagacc atcccggtgg agaccatcga gaccacagtg    360
gtgggcgagg aggagg                                                    376
```

```
<210> SEQ ID NO 3
<211> LENGTH: 288
<212> TYPE: DNA
<213> ORGANISM: Artificial
<220> FEATURE:
<223> OTHER INFORMATION: IL-10
<220> FEATURE:
<221> NAME/KEY: misc_feature
<222> LOCATION: (16)..(18)
<223> OTHER INFORMATION: target sequence for hammerhead ribozyme
<220> FEATURE:
<221> NAME/KEY: misc_feature
<222> LOCATION: (31)..(33)
<223> OTHER INFORMATION: starting Met
<220> FEATURE:
<221> NAME/KEY: misc_feature
<222> LOCATION: (39)..(41)
<223> OTHER INFORMATION: target sequence for hammerhead ribozyme
<220> FEATURE:
<221> NAME/KEY: misc_feature
<222> LOCATION: (53)..(55)
<223> OTHER INFORMATION: target sequence for hammerhead ribozyme
<220> FEATURE:
<221> NAME/KEY: misc_feature
<222> LOCATION: (61)..(63)
<223> OTHER INFORMATION: target sequence for hammerhead ribozyme
<220> FEATURE:
<221> NAME/KEY: misc_feature
<222> LOCATION: (100)..(138)
<223> OTHER INFORMATION: complementary sequence of the hairpin ribozyme
<220> FEATURE:
<221> NAME/KEY: misc_feature
<222> LOCATION: (103)..(107)
<223> OTHER INFORMATION: target sequence for a chosen ribozyme
<220> FEATURE:
<221> NAME/KEY: misc_feature
<222> LOCATION: (103)..(103)
<223> OTHER INFORMATION: target sequence for both hammerhead and hairpin
      ribozymes
<220> FEATURE:
<221> NAME/KEY: misc_feature
<222> LOCATION: (105)..(107)
<223> OTHER INFORMATION: target sequence for both hammerhead and hairpin
      ribozymes
<220> FEATURE:
<221> NAME/KEY: misc_feature
<222> LOCATION: (232)..(232)
<223> OTHER INFORMATION: target sequence for both hammerhead and hairpin
      ribozymes
<220> FEATURE:
<221> NAME/KEY: misc_feature
<222> LOCATION: (234)..(236)
<223> OTHER INFORMATION: target sequence for both hammerhead and hairpin
      ribozymes

<400> SEQUENCE: 3
aaaccacaag acagacttgc aaaagaaggc atgcacagct cagcactgct ctgttgcctg    60
gtcctcctga ctggggtgag ggccagccca ggccagggca cccagtctga aacagctgc    120 acccacttcc caggcaacct gcctaacatg cttcgagatc tccgagatgc cttcagcaga    180
gtgaagactt tctttcaaat gaaggatcag ctggacaact tgttgttaaa ggagtccttg    240
```
ctggaggact ttaagggtta cctgggttgc aagccttgt ctgagatg        288

<210> SEQ ID NO 4
<211> LENGTH: 296
<212> TYPE: DNA
<213> ORGANISM: Artificial
<220> FEATURE:
<223> OTHER INFORMATION: COX2
<220> FEATURE:
<221> NAME/KEY: misc_feature
<222> LOCATION: (10)..(15)
<223> OTHER INFORMATION: target sequence for hammerhead ribozyme
<220> FEATURE:
<221> NAME/KEY: misc_feature
<222> LOCATION: (24)..(26)
<223> OTHER INFORMATION: target sequence for hammerhead ribozyme
<220> FEATURE:
<221> NAME/KEY: misc_feature
<222> LOCATION: (28)..(30)
<223> OTHER INFORMATION: target sequence for hammerhead ribozyme
<220> FEATURE:
<221> NAME/KEY: misc_feature
<222> LOCATION: (33)..(35)
<223> OTHER INFORMATION: target sequence for hammerhead ribozyme
<220> FEATURE:
<221> NAME/KEY: misc_feature
<222> LOCATION: (50)..(52)
<223> OTHER INFORMATION: target sequence for hammerhead ribozyme
<220> FEATURE:
<221> NAME/KEY: misc_feature
<222> LOCATION: (98)..(100)
<223> OTHER INFORMATION: starting Met
<220> FEATURE:
<221> NAME/KEY: misc_feature
<222> LOCATION: (101)..(103)
<223> OTHER INFORMATION: target sequence for hammerhead ribozyme
<220> FEATURE:
<221> NAME/KEY: misc_feature
<222> LOCATION: (123)..(159)
<223> OTHER INFORMATION: complementary sequence of the hairpin ribozyme
<220> FEATURE:
<221> NAME/KEY: misc_feature
<222> LOCATION: (126)..(130)
<223> OTHER INFORMATION: target sequence for a chosen ribozyme
<220> FEATURE:
<221> NAME/KEY: misc_feature
<222> LOCATION: (126)..(126)
<223> OTHER INFORMATION: target sequence for both hammerhead and hairpin
      ribozymes
<220> FEATURE:
<221> NAME/KEY: misc_feature
<222> LOCATION: (128)..(130)
<223> OTHER INFORMATION: target sequence for both hammerhead and hairpin
      ribozymes
<220> FEATURE:
<221> NAME/KEY: misc_feature
<222> LOCATION: (162)..(164)
<223> OTHER INFORMATION: target sequence for hammerhead ribozyme

<400> SEQUENCE: 4
gtccaggaac tcctcagcag cgcctccttc agctccacag ccagacgccc tcagacagca    60
aagcctaccc ccgcgccgcg ccctgcccgc cgctgcgatg ctcgcccgcg ccctgctgct   120
gtgcgcggtc ctggcgctca gccatacagc aaatccttgc tgttcccacc catgtcaaaa   180
ccgaggtgta tgtatgagtg tgggatttga ccagtataag tgcgattgta cccggacagg   240
attctatgga gaaaactgct caacaccgga attttgaca agaataaaat tatttc        296

<210> SEQ ID NO 5
<211> LENGTH: 54
<212> TYPE: DNA
<213> ORGANISM: Artificial
<220> FEATURE:
<223> OTHER INFORMATION: Ad2 Stuffer (nts. 1051-10584)

```
<400> SEQUENCE: 5
ccatggtcgg gacgctctgg ccggtgaggc gtgcgcagtc gttgacgctc tgga            54

<210> SEQ ID NO 6
<211> LENGTH: 98
<212> TYPE: DNA
<213> ORGANISM: Artificial
<220> FEATURE:
<223> OTHER INFORMATION: Ad2 VA1RNA promoter [(-70/+30) (nts.
      10585-10682)]

<400> SEQUENCE: 6
ccgtgcaaaa ggagagcctg taagcgggca ctcttccgtg gtctggtgga taaattcgca    60
agggtatcat ggcggacgac cggggttcga accccgga                             98

<210> SEQ ID NO 7
<211> LENGTH: 101
<212> TYPE: DNA
<213> ORGANISM: Artificial
<220> FEATURE:
<223> OTHER INFORMATION: Rhinovirus 1A 3C Protease  (nts. 447-457)

<400> SEQUENCE: 7
cctaaaacca aagtacctga agaagagta gttgctcaag gtccagaaga agaatttgga    60
aggtcaattc tcaaaaacaa tacttgtgtg attactacag g                        101

<210> SEQ ID NO 8
<211> LENGTH: 10
<212> TYPE: DNA
<213> ORGANISM: Artificial
<220> FEATURE:
<223> OTHER INFORMATION: stem

<400> SEQUENCE: 8
cccccccccc                                                           10

<210> SEQ ID NO 9
<211> LENGTH: 101
<212> TYPE: DNA
<213> ORGANISM: Artificial
<220> FEATURE:
<223> OTHER INFORMATION: Rhinovirus 1A 3C Protease  (nts. 447-457)
      ANTISENSE

<400> SEQUENCE: 9
cctgtagtaa tcacacaagt attgttttg agaattgacc ttccaaattc ttcttctgga    60
ccttgagcaa ctactcttct ttcaggtact ttggttttag g                        101

<210> SEQ ID NO 10
<211> LENGTH: 13
<212> TYPE: DNA
<213> ORGANISM: Artificial
<220> FEATURE:
<223> OTHER INFORMATION: RNA polymerase III termination sequence

<400> SEQUENCE: 10 gcgcttttg cgc                                                        13

<210> SEQ ID NO 11
<211> LENGTH: 78
<212> TYPE: DNA
<213> ORGANISM: Artificial
<220> FEATURE:
```

<223> OTHER INFORMATION: Ad2VA 1F

<400> SEQUENCE: 11
agatctccat ggtcgggacg ctctggccgg tgaggcgtgc gcagtcgttg acgctctgga    60
ccgtgcaaaa ggagagcc                                                  78

<210> SEQ ID NO 12
<211> LENGTH: 58
<212> TYPE: DNA
<213> ORGANISM: Artificial
<220> FEATURE:
<223> OTHER INFORMATION: Ad2VA 1R

<400> SEQUENCE: 12
cccttgcgaa tttatccacc agaccacgga agagtgcccg cttacaggct ctcctttt     58

<210> SEQ ID NO 13
<211> LENGTH: 79
<212> TYPE: DNA
<213> ORGANISM: Artificial
<220> FEATURE:
<223> OTHER INFORMATION: Ad2VA 2F

<400> SEQUENCE: 13
aattcgcaag ggtatcatgg cggacgaccg gggttcgaac cccggatcta gacctaaaac    60
caaagtacct gaaagaaga                                                 79

<210> SEQ ID NO 14
<211> LENGTH: 58
<212> TYPE: DNA
<213> ORGANISM: Artificial
<220> FEATURE:
<223> OTHER INFORMATION: Ad2VA 2R

<400> SEQUENCE: 14
tgagaattga ccttccaaat tcttcttctg gaccttgagc aactactctt ctttcagg     58

<210> SEQ ID NO 15
<211> LENGTH: 79
<212> TYPE: DNA
<213> ORGANISM: Artificial
<220> FEATURE:
<223> OTHER INFORMATION: Ad2VA 3F

<400> SEQUENCE: 15
ggtcaattct caaaaacaat acttgtgtga ttactacagg cccccccccc cctgtagtaa    60
tcacacaagt attgttttt                                                 79

<210> SEQ ID NO 16
<211> LENGTH: 58
<212> TYPE: DNA
<213> ORGANISM: Artificial
<220> FEATURE:
<223> OTHER INFORMATION: Ad2VA 3R

<400> SEQUENCE: 16
agtagttgct caaggtccag aagaagaatt tggaaggtca attctcaaaa acaatact     58

<210> SEQ ID NO 17
<211> LENGTH: 69
<212> TYPE: DNA
<213> ORGANISM: Artificial
<220> FEATURE:
<223> OTHER INFORMATION: Ad2VA 4F

<400> SEQUENCE: 17
tgagcaacta ctcttctttc aggtactttg gttttaggga attcgcgctt tttgcgctcc    60
ggaagatct                                                             69

<210> SEQ ID NO 18
<211> LENGTH: 22
<212> TYPE: DNA
<213> ORGANISM: Artificial
<220> FEATURE:
<223> OTHER INFORMATION: Ad2VA 4R

<400> SEQUENCE: 18
agatcttccg gagcgcaaaa ag                                              22

<210> SEQ ID NO 19
<211> LENGTH: 28
<212> TYPE: DNA
<213> ORGANISM: Artificial
<220> FEATURE:
<223> OTHER INFORMATION: Ad2 PCR 1F

<400> SEQUENCE: 19
cccttcccag atctccatgg tcgggacg                                        28

<210> SEQ ID NO 20
<211> LENGTH: 30
<212> TYPE: DNA
<213> ORGANISM: Artificial
<220> FEATURE:
<223> OTHER INFORMATION: Ad2 PCR 1R

<400> SEQUENCE: 20
tttcctttag atcttccgga gcgcaaaaag                                      30

<210> SEQ ID NO 21
<211> LENGTH: 37
<212> TYPE: DNA
<213> ORGANISM: Artificial
<220> FEATURE:
<223> OTHER INFORMATION: BAXafwd

<400> SEQUENCE: 21
atatatgaat tcggtgatgg acgggtccgg ggagcag                              37

<210> SEQ ID NO 22
<211> LENGTH: 37
<212> TYPE: DNA
<213> ORGANISM: Artificial
<220> FEATURE:
<223> OTHER INFORMATION: BAXarev

<400> SEQUENCE: 22
tatatagaat tctcagccca tcttcttcca gatggtg                              37

<210> SEQ ID NO 23
<211> LENGTH: 54
<212> TYPE: DNA
<213> ORGANISM: Artificial
<220> FEATURE:
<223> OTHER INFORMATION: Ad2 Stuffer (nts. 1051-10584)

<400> SEQUENCE: 23
ccatggtcgg gacgctctgg ccggtgaggc gtgcgcagtc gttgacgctc tgga           54

<210> SEQ ID NO 24
<211> LENGTH: 98
<212> TYPE: DNA
<213> ORGANISM: Artificial
<220> FEATURE:
<223> OTHER INFORMATION: Ad2 VA1RNA promoter [(-70/+30) (nts. 10585-10682)]

<400> SEQUENCE: 24
ccgtgcaaaa ggagagcctg taagcgggca ctcttccgtg gtctggtgga taaattcgca        60
agggtatcat ggcggacgac cggggttcga accccgga        98

<210> SEQ ID NO 25
<211> LENGTH: 41
<212> TYPE: DNA
<213> ORGANISM: Artificial
<220> FEATURE:
<223> OTHER INFORMATION: Human Bcl-2 coding sequence comprising nucleotides 4-44

<400> SEQUENCE: 25
gcgcacgctg ggagaacggg gtacgacaac cgggagatag t        41

<210> SEQ ID NO 26
<211> LENGTH: 13
<212> TYPE: DNA
<213> ORGANISM: Artificial
<220> FEATURE:
<223> OTHER INFORMATION: RNA polymerase III termination sequence

<400> SEQUENCE: 26 gcgcttttg cgc        13

<210> SEQ ID NO 27
<211> LENGTH: 77
<212> TYPE: DNA
<213> ORGANISM: Artificial
<220> FEATURE:
<223> OTHER INFORMATION: Ad2VAbcl 1F

<400> SEQUENCE: 27
gaattccatg gtcgggacgc tctggccggt gaggcgtgcg cagtcgttga cgctctggac        60
cgtgcaaaag gagagcc        77

<210> SEQ ID NO 28
<211> LENGTH: 58
<212> TYPE: DNA
<213> ORGANISM: Artificial
<220> FEATURE:
<223> OTHER INFORMATION: Ad2VAbcl 1R

<400> SEQUENCE: 28
cccttgcgaa tttatccacc agaccacgga agagtgcccg cttacaggct ctccttt        58

<210> SEQ ID NO 29
<211> LENGTH: 74
<212> TYPE: DNA
<213> ORGANISM: Artificial
<220> FEATURE:
<223> OTHER INFORMATION: Ad2VAbcl 2F

<400> SEQUENCE: 29
aattcgcaag ggtatcatgg cggacgaccg gggttcgaac cccggaacta tctcccggtt        60
gtcgtacccc gttc        74

<210> SEQ ID NO 30
<211> LENGTH: 45
<212> TYPE: DNA
<213> ORGANISM: Artificial
<220> FEATURE:
<223> OTHER INFORMATION: Ad2VAbcl 2R

<400> SEQUENCE: 30
gaattcgcgc aaaaagcgcg cgcacgctgg gagaacgggg tacga                45

<210> SEQ ID NO 31
<211> LENGTH: 27
<212> TYPE: DNA
<213> ORGANISM: Artificial
<220> FEATURE:
<223> OTHER INFORMATION: AdVA PCR 1F

<400> SEQUENCE: 31
atatatagaa ttccatggtc gggacgc                                    27

<210> SEQ ID NO 32
<211> LENGTH: 25
<212> TYPE: DNA
<213> ORGANISM: Artificial
<220> FEATURE:
<223> OTHER INFORMATION: AdVA PCR 1R

<400> SEQUENCE: 32
atatatgaat tcgcgcaaaa agcgc                                      25

<210> SEQ ID NO 33
<211> LENGTH: 74
<212> TYPE: DNA
<213> ORGANISM: Artificial
<220> FEATURE:
<223> OTHER INFORMATION: Ad2VAbcl 3F

<400> SEQUENCE: 33
aattcgcaag ggtatcatgg cggacgaccg gggttcgaac cccggagcgc acgctgggag    60
aacggggtac gaca                                                    74

<210> SEQ ID NO 34
<211> LENGTH: 45
<212> TYPE: DNA
<213> ORGANISM: Artificial
<220> FEATURE:
<223> OTHER INFORMATION: Ad2VAbcl 3R

<400> SEQUENCE: 34
gaattcgcgc aaaaagcgca ctatctcccg gttgtcgtac cccgt                 45

<210> SEQ ID NO 35
<211> LENGTH: 54
<212> TYPE: DNA
<213> ORGANISM: Artificial
<220> FEATURE:
<223> OTHER INFORMATION: Ad2 Stuffer (nts. 1051-10584)

<400> SEQUENCE: 35
ccatggtcgg gacgctctgg ccggtgaggc gtgcgcagtc gttgacgctc tgga       54

<210> SEQ ID NO 36
<211> LENGTH: 98
<212> TYPE: DNA

<213> ORGANISM: Artificial
<220> FEATURE:
<223> OTHER INFORMATION: Ad2 VA1RNA promoter [(-70/+30) (nts.
10585-10682)]

<400> SEQUENCE: 36

```
ccgtgcaaaa ggagagcctg taagcgggca ctcttccgtg gtctggtgga taaattcgca      60
agggtatcat ggcggacgac cggggttcga accccgga                              98
```

<210> SEQ ID NO 37
<211> LENGTH: 63
<212> TYPE: DNA
<213> ORGANISM: Artificial
<220> FEATURE:
<223> OTHER INFORMATION: IRF2 specific ribozyme

<400> SEQUENCE: 37

```
ctcagtgtgc ttttttcacg cctgatgagg ccgtgaggcc gaaaccaata caattccgca      60
agg                                                                    63
```

<210> SEQ ID NO 38
<211> LENGTH: 13
<212> TYPE: DNA
<213> ORGANISM: Artificial
<220> FEATURE:
<223> OTHER INFORMATION: RNA polymerase III termination sequence

<400> SEQUENCE: 38

```
gcgcttttttg cgc                                                        13
```

<210> SEQ ID NO 39
<211> LENGTH: 56
<212> TYPE: DNA
<213> ORGANISM: Artificial
<220> FEATURE:
<223> OTHER INFORMATION: VAIRF2-1F

<400> SEQUENCE: 39

```
cacacactta attaaccatg gtcgggacgc tctggccggt gaggcgtgcg cagtcg          56
```

<210> SEQ ID NO 40
<211> LENGTH: 55
<212> TYPE: DNA
<213> ORGANISM: Artificial
<220> FEATURE:
<223> OTHER INFORMATION: VAIRF2-1R

<400> SEQUENCE: 40

```
ccgcttacag gctctccttt tgcacggtcc agagcgtcaa cgactgcgca cgcct           55
```

<210> SEQ ID NO 41
<211> LENGTH: 55
<212> TYPE: DNA
<213> ORGANISM: Artificial
<220> FEATURE:
<223> OTHER INFORMATION: VAIRF2-2F

<400> SEQUENCE: 41

```
agagcctgta agcgggcact cttccgtggt ctggtggata aattcgcaag ggtat           55
```

<210> SEQ ID NO 42
<211> LENGTH: 55
<212> TYPE: DNA
<213> ORGANISM: Artificial
<220> FEATURE:

-continued

<223> OTHER INFORMATION: VAIRF2-2R

<400> SEQUENCE: 42
cacactgagt ccggggttcg aaccccggtc gtccgccatg ataccettgc gaatt    55

<210> SEQ ID NO 43
<211> LENGTH: 55
<212> TYPE: DNA
<213> ORGANISM: Artificial
<220> FEATURE:
<223> OTHER INFORMATION: VAIRF2-3F

<400> SEQUENCE: 43
cccggactca gtgtgctttt ttcacgcctg atgaggccgt gaggccgaaa ccaat    55

<210> SEQ ID NO 44
<211> LENGTH: 56
<212> TYPE: DNA
<213> ORGANISM: Artificial
<220> FEATURE:
<223> OTHER INFORMATION: VAIRF2-3R

<400> SEQUENCE: 44
gtgtgtttaa ttaagcgcaa aaagcgccct tgcggaattg tattggtttc ggcctc    56

<210> SEQ ID NO 45
<211> LENGTH: 54
<212> TYPE: DNA
<213> ORGANISM: Artificial
<220> FEATURE:
<223> OTHER INFORMATION: Ad2 Stuffer (nts. 1051-10584)

<400> SEQUENCE: 45
ccatggtcgg gacgctctgg ccggtgaggc gtgcgcagtc gttgacgctc tgga    54

<210> SEQ ID NO 46
<211> LENGTH: 98
<212> TYPE: DNA
<213> ORGANISM: Artificial
<220> FEATURE:
<223> OTHER INFORMATION: Ad2 VA1RNA promoter [(-70/+30) (nts.
      10585-10682)]

<400> SEQUENCE: 46
ccgtgcaaaa ggagagcctg taagcgggca ctcttccgtg gtctggtgga taaattcgca    60
agggtatcat ggcggacgac cggggttcga accccgga    98

<210> SEQ ID NO 47
<211> LENGTH: 74
<212> TYPE: DNA
<213> ORGANISM: Artificial
<220> FEATURE:
<223> OTHER INFORMATION: COX2 specific ribozyme

<400> SEQUENCE: 47
gcaaggattt gctgtatggc tgagcgccag agaagcgcac cagagaaaca cacgttgtgg    60
tatattacct ggta    74

<210> SEQ ID NO 48
<211> LENGTH: 13
<212> TYPE: DNA
<213> ORGANISM: Artificial
<220> FEATURE:
<223> OTHER INFORMATION: RNA polymerase III termination sequence

```
<400> SEQUENCE: 48 gcgcttttg cgc                                                        13

<210> SEQ ID NO 49
<211> LENGTH: 57
<212> TYPE: DNA
<213> ORGANISM: Artificial
<220> FEATURE:
<223> OTHER INFORMATION: VACOX2-1F

<400> SEQUENCE: 49
cacacattaa ttaaccatgg tcgggacgct ctggccggtg aggcgtgcgc agtcgtt      57

<210> SEQ ID NO 50
<211> LENGTH: 57
<212> TYPE: DNA
<213> ORGANISM: Artificial
<220> FEATURE:
<223> OTHER INFORMATION: VACOX2-1R

<400> SEQUENCE: 50
gtgcccgctt acaggctctc cttttgctcg gtccagagcg tcaacgactg cgcacgc      57

<210> SEQ ID NO 51
<211> LENGTH: 57
<212> TYPE: DNA
<213> ORGANISM: Artificial
<220> FEATURE:
<223> OTHER INFORMATION: VACOX2-2F

<400> SEQUENCE: 51
cctgtaagcg ggcactcttc cgtggtctgg tggataaatt cgcaagggta tcatggc      57

<210> SEQ ID NO 52
<211> LENGTH: 57
<212> TYPE: DNA
<213> ORGANISM: Artificial
<220> FEATURE:
<223> OTHER INFORMATION: VACOX2-2R

<400> SEQUENCE: 52
atacagcaaa tccttgctcc ggggttcgaa ccccggtcgt ccgccatgat acccttg      57

<210> SEQ ID NO 53
<211> LENGTH: 57
<212> TYPE: DNA
<213> ORGANISM: Artificial
<220> FEATURE:
<223> OTHER INFORMATION: VACOX2-3F

<400> SEQUENCE: 53
aaggatttgc tgtatggctg agcgccagag aagcgcacca gagaaacaca cgttgtg      57

<210> SEQ ID NO 54
<211> LENGTH: 57
<212> TYPE: DNA
<213> ORGANISM: Artificial
<220> FEATURE:
<223> OTHER INFORMATION: VACOX2-3R

<400> SEQUENCE: 54
tgtgtgttaa ttaagcgcaa aaagcgctac caggtaatat accacaacgt gtgtttc      57

<210> SEQ ID NO 55
<211> LENGTH: 55
```

<212> TYPE: DNA
<213> ORGANISM: Artificial
<220> FEATURE:
<223> OTHER INFORMATION: VAYY1-1F

<400> SEQUENCE: 55
cacacactta attaaccatg gtcgggacgc tctggccggt gaggcgtgcg cagtc        55

<210> SEQ ID NO 56
<211> LENGTH: 55
<212> TYPE: DNA
<213> ORGANISM: Artificial
<220> FEATURE:
<223> OTHER INFORMATION: VAIYY1-1R

<400> SEQUENCE: 56
cgcttacagg ctctcctttt gcacggtcca gagcgtcaac gactgcgcac gcctc        55

<210> SEQ ID NO 57
<211> LENGTH: 55
<212> TYPE: DNA
<213> ORGANISM: Artificial
<220> FEATURE:
<223> OTHER INFORMATION: VAIYY1-2F

<400> SEQUENCE: 57
gagagcctgt aagcgggcac tcttccgtgg tctggtggat aaattcgcaa gggta        55

<210> SEQ ID NO 58
<211> LENGTH: 55
<212> TYPE: DNA
<213> ORGANISM: Artificial
<220> FEATURE:
<223> OTHER INFORMATION: VAIYY1-2R

<400> SEQUENCE: 58
ctacatcgtc cggggttcga accccggtcg tccgccatga tacccttgcg aattt        55

<210> SEQ ID NO 59
<211> LENGTH: 55
<212> TYPE: DNA
<213> ORGANISM: Artificial
<220> FEATURE:
<223> OTHER INFORMATION: VAIYY1-3F

<400> SEQUENCE: 59
ccccggacga tgtagagggt gtcgcccctg atgaggccgt gaggccgaaa ggcca        55

<210> SEQ ID NO 60
<211> LENGTH: 55
<212> TYPE: DNA
<213> ORGANISM: Artificial
<220> FEATURE:
<223> OTHER INFORMATION: VAIRF2-3R

<400> SEQUENCE: 60
gtgtgtttaa ttaagcgcaa aaagcgcgag ccctcagcca tggcctttcg gcctc        55

<210> SEQ ID NO 61
<211> LENGTH: 58
<212> TYPE: DNA
<213> ORGANISM: Artificial
<220> FEATURE:
<223> OTHER INFORMATION: VAIL10-1F

<400> SEQUENCE: 61

-continued cacacattaa ttaaccatgg tcgggacgct ctggccggtg aggcgtgcgc agtcgttg    58

<210> SEQ ID NO 62
<211> LENGTH: 57
<212> TYPE: DNA
<213> ORGANISM: Artificial
<220> FEATURE:
<223> OTHER INFORMATION: VAIL10-1R

<400> SEQUENCE: 62
agtgcccgct tacaggctct cctttgcac ggtccagagc gtcaacgact gcgcacg    57

<210> SEQ ID NO 63
<211> LENGTH: 57
<212> TYPE: DNA
<213> ORGANISM: Artificial
<220> FEATURE:
<223> OTHER INFORMATION: VAIL10-2F

<400> SEQUENCE: 63
ctgtaagcgg gcactcttcc gtggtctggt ggataaattc gcaagggtat catggcg    57

<210> SEQ ID NO 64
<211> LENGTH: 57
<212> TYPE: DNA
<213> ORGANISM: Artificial
<220> FEATURE:
<223> OTHER INFORMATION: VAIL10-2R

<400> SEQUENCE: 64
cccacttccc aggcaacctc cggggttcga accccggtcg tccgccatga taccctt    57

<210> SEQ ID NO 65
<211> LENGTH: 57
<212> TYPE: DNA
<213> ORGANISM: Artificial
<220> FEATURE:
<223> OTHER INFORMATION: VAIL10-3F

<400> SEQUENCE: 65
tgcctgggaa gtgggtgcag ctgttctcaa gaagggtacc agagaaacac acgttgt    57

<210> SEQ ID NO 66
<211> LENGTH: 58
<212> TYPE: DNA
<213> ORGANISM: Artificial
<220> FEATURE:
<223> OTHER INFORMATION: VAIL10-3R

<400> SEQUENCE: 66
tgtgtgttaa ttaagcgcaa aaagcgctac caggtaatat accacaacgt gtgttct    58

<210> SEQ ID NO 67
<211> LENGTH: 36
<212> TYPE: DNA
<213> ORGANISM: Artificial
<220> FEATURE:
<223> OTHER INFORMATION: Her2neuFwd

<400> SEQUENCE: 67
atatatatct agacaccatg gagctggcgg ccttgt    36

<210> SEQ ID NO 68
<211> LENGTH: 37
<212> TYPE: DNA
<213> ORGANISM: Artificial

-continued

```
<220> FEATURE:
<223> OTHER INFORMATION: Her2neuRev

<400> SEQUENCE: 68
tatatagcgg ccgctcacac tggcacgtcc agaccca                                37

<210> SEQ ID NO 69
<211> LENGTH: 40
<212> TYPE: DNA
<213> ORGANISM: Artificial
<220> FEATURE:
<223> OTHER INFORMATION: gp100Fwd

<400> SEQUENCE: 69
atatatatct agacacaatg gatctggtgc taaaaagatg                             40

<210> SEQ ID NO 70
<211> LENGTH: 38
<212> TYPE: DNA
<213> ORGANISM: Artificial
<220> FEATURE:
<223> OTHER INFORMATION: gp100Rev

<400> SEQUENCE: 70
tatatagcgg ccgctcagac ctgctgccca ctgaggag                               38
```

ENHANCEMENT OF THE IMMUNE RESPONSE FOR VACCINE AND GENE THERAPY APPLICATIONS

CROSS-REFERENCE TO RELATED APPLICATIONS

This application is a division of Ser. No. 09/546,201 filed Apr. 10, 2000, which claims priority to U.S. Provisional Application No. 60/128,409, filed Apr. 8, 1999. These applications are incorporated by reference herein in their entireties.

This application incorporates by reference the contents of a 19.6 KB text file labeled "PP001463_sequence_listing.txt" and created Apr. 29, 2008, which is the sequence listing for this application.

TECHNICAL FIELD

The present invention relates generally to pharmaceutical compositions and methods, and more specifically, to a variety of compositions and methods suitable for increasing, enhancing, or stimulating an immune response, particularly for prophylactic and therapeutic vaccine applications in the areas of infectious disease and cancer.

BACKGROUND OF THE INVENTION

Substantial research has been undertaken in order to realize the possibility that the course of disease may be affected through the introduction of nucleic acids into living organisms. When utilized for medical purposes, such therapy, termed "gene therapy", allows the alteration of the genetic repertoire of cells for a therapeutic benefit.

A variety of methods have been described for delivering nucleic acids to cells, including for example, the use of viral vectors derived from retrovirus, adenovirus, poxvirus, herpes virus, and adeno-associated virus (see Jolly, *Cancer Gene Therapy* 1:51-64, 1994), as well as direct nucleic acid transfer techniques, including direct DNA injection (Donnelly, J. J. et al., *Ann. Rev. Immunol.* 15:617-648, 1997), micro-projectile bombardment (Williams et al., *PNAS* 88:2726-2730, 1991), and nucleic acid complexes with lipids of several types (Felgner et al., *Proc. Natl. Acad. Sci. USA* 84:7413-7417, 1989). Many of these strategies are being applied widely, with clinical trials now ongoing for a wide range of hereditary (e.g., ADA deficiency, cystic fibrosis, hemophilia) and acquired (e.g., cancer, viral infection) diseases (Crystal, *Science* 270: 404-410, 1995).

One particularly important application of gene therapy is in the vaccine field. Briefly, live virus vaccines (e.g., vaccinia, polio, measles) have been enormously successful and have made a dramatic and historic impact on public health. However, for certain pathogens, such as HIV, safety concerns about either reversion of attenuated vaccine strains to virulent phenotypes or inducing fulminate infection in immune compromised individuals have forced the development of subunit or inactivated virus vaccines. Unfortunately, in many cases, these vaccines have not elicited the potent broad-based humoral, cellular, and mucosal immune responses or long-term memory necessary to confer life-long protection in immunized individuals. Induction of such robust immune responses will be particularly important for vaccines against HIV and HCV infection, both of which have reached worldwide epidemic proportions and have, to date, proved elusive to candidate vaccines.

Still relatively new, plasmid DNA-based vaccines combine the latest developments of molecular biology with an ever-increasing understanding of immunology, and show promise for immunization against infection with pathogens, such as HIV, as well as other diseases for which improved vaccines are needed (e.g., influenza virus). Importantly, DNA immunization elicits humoral and cellular immune responses in rodents and non-human primates. DNA is an attractive mode for vaccination, as it provides the safety advantages of subunit or inactivated virus vaccines, and induces the MHC class I-restricted cytotoxic T cell responses typical of live virus, or "replicating antigen" vaccines, which may be critical for efficacy (Donnelly, J. J. et al., ibid).

Unfortunately however, recent DNA vaccine clinical trials have demonstrated that, although antigen-specific cytotoxic T lymphocyte responses were observed in vaccinated individuals, these responses were insufficient to afford protection against challenge with the infectious agent (Wang, R. et al., *Science* 282:476-480, 1998; Calarota, S. et al., *Lancet* 351: 1320-1325, 1998). Thus, for DNA-based vaccination to become a widely used method for protection against infectious disease and cancer, the technology must be further improved.

The present invention provides compositions and methods for enhancing the efficacy of DNA vectors, as well as a variety of other gene delivery vectors, used for genetic immunization. Such improvements can include immunostimulatory modifications to the antigen-expressing vector itself, or the in vivo administration, along with the antigen-expressing vector, of one or more additional gene delivery vectors that are immunostimulatory. The improvements described herein address previous difficulties associated with the use of gene delivery vectors by enhancing the extent of the antigen-specific immune response, thus providing the broad and robust responses critical for successful prophylactic or therapeutic vaccination against infectious agents and cancer.

SUMMARY OF THE INVENTION

Briefly stated, the present invention provides compositions and methods suitable for increasing, enhancing, or stimulating an immune response. For example, within one aspect of the invention expression cassettes are provided comprising a promoter operably linked to a nucleic acid molecule which, when transcribed in vivo, forms double stranded RNA that induces the production of interferon (alpha, beta, or gamma) either directly or indirectly, which in turn may upregulate MHC Class I and/or Class II molecules, thereby stimulating an immune response.

Within one aspect of the present invention, expression cassettes are provided comprising a promoter operably linked to a nucleic acid molecule which, when transcribed in vivo, forms double stranded RNA that induces the production of interferon, wherein the expression cassette is selected from the group consisting of: (a) an expression cassette which, when transcribed in vivo, forms self-complementary RNA; and (b) an expression cassette comprising a first promoter operably linked to a first nucleic acid molecule, and a second promoter operably linked to a second nucleic acid molecule, wherein the first and second nucleic acid molecules, when transcribed in vivo, form double stranded RNA that induces the production of interferon. Within various embodiments of the invention, the RNA may be either coding or non-coding.

Within other aspects of the invention, expression cassettes are provided comprising a promoter operably linked to a ribozyme or antisense nucleic acid molecule which, when transcribed in vivo, forms a ribozyme or antisense RNA molecule that stimulates an immune response. Within one embodiment, the ribozyme or antisense molecule inhibits expression of a protein that can inhibit at least one aspect of an immune response. Representative examples of suitable proteins that may be inhibited according to the present invention include IRF2, YY1, IL-10, TGF-β and cyclooxygenase. It should be noted that inhibition of protein expression may in certain instances occur by binding and/or cleavage of mRNA by the ribozyme or antisense molecule.

Within another aspect, expression cassettes are provided comprising a promoter operably linked to a ribozyme or antisense nucleic acid molecule which, when transcribed in vivo, stimulates apoptosis. Representative examples of suitable ribozymes or antisense molecules include those that cleave or inhibit targets within an apoptosis cascade, including for example, Bcl-2 and Bcl-xL.

Within other aspects, expression cassettes are provided comprising a first promoter operably linked to a nucleic acid molecule which, when transcribed in vivo, forms double stranded RNA that induces the production of interferon, and a second promoter operably linked to a nucleic acid molecule that encodes an antigen from a pathogenic agent. Within yet other aspects, expression cassettes are provided comprising a first promoter operably linked to a ribozyme or antisense nucleic acid molecule which, when transcribed in vivo, stimulates apoptosis, and a second promoter operably linked to a nucleic acid molecule that encodes an antigen from a pathogenic agent. Within certain embodiments, the pathogenic agent is a virus, bacteria, fungus, parasite or cancerous cell. In a further aspect, expression cassettes are provided which direct the expression of both a polypeptide that promotes apoptosis and an antigen from a pathogenic agent. Within certain embodiments, the antigen from the pathogenic agent and the polypeptide that promotes apoptosis are expressed from separate promoters. Representative examples of pro-apoptotic polypeptides include Bax, Bik, Bcl-xL. Alternatively, the polypeptide and antigen can be transcribed from the same promoter and expressed by an Internal Ribosome Entry Site or ribosome readthrough.

Within various embodiments, any of the above expression cassettes may contain an RNA polymerase I, RNA polymerase II (e.g., CMV, SV40, MoMLV LTR and RSV LTR), or RNA polymerase III promoter (e.g., an Adenovirus VA1 promoter).

Within certain embodiments of the invention, the above noted expression cassettes may further comprise an additional promoter operably linked to a nucleic acid molecule that encodes a polypeptide of interest. Within certain embodiments, the promoter is a RNA polymerase II promoter (e.g., CMV, SV40, MoMLV LTR and RSV LTR). A wide variety of polypeptides may be expressed, including for example polypeptides that promote apoptosis, antigens from a pathogenic agent, prodrug converting enzymes, and cytokines (e.g., gamma interferon, IL-2, IL-12, and IL-15). Pathogenic agents can include viruses (e.g., HIV, HSV, HBV, HCV, HPV, and FIV), bacteria, parasites, fungus and tumors.

Within related aspects, the present invention further provides gene delivery vectors that contain one or more of the expression cassettes described herein. Representative examples of gene delivery vectors include plasmids and recombinant viral vectors derived from retrovirus, herpesvirus, poxvirus, adenovirus, AAV, parvovirus, alphavirus, polyoma virus, and vesiculovirus.

Expression cassettes and gene delivery vehicles as described herein can be transformed, transfected or otherwise introduced into a wide variety of host cells, including for example, a wide variety of vertebrate cells (e.g., mammalian cells such as human, non-human primate, horse, dog, mouse).

Expression cassettes and gene delivery vehicles as provided herein can be utilized to stimulate an immune response within a desired host, comprising the general step of administering to an animal an expression cassette or gene delivery vector as described herein, such that an immune response is generated.

These and other aspects of the present invention will become evident upon reference to the following detailed description and attached drawings. In addition, various references are set forth herein which describe in more detail certain procedures or compositions (e.g., DNA constructs), and are therefore incorporated by reference in their entirety.

BRIEF DESCRIPTION OF THE DRAWINGS

FIG. 6 depicts several target cleavage sites in IRF2 (SEQ ID NO: 1), YY1 (SEQ ID NO:2), IL-10 (SEQ ID NO:3) and Cox2 (SEQ ID NO:4) mRNA. The right-angled arrow depicts the starting methionine. The double-sided arrows with solid lines depict complementary sequence for the hammerhead ribozyme. The double-sided arrows with broken lines depict complementary sequence of the hairpin ribozyme. The boxed sequences are target sequences for a chosen ribozyme. Sequences in bold are target sequences for hammerhead ribozyme and sequences in bold and underlined are target sequences for both hammerhead and hairpin ribozymes.

DETAILED DESCRIPTION OF THE INVENTION

Definitions

Figure 1:
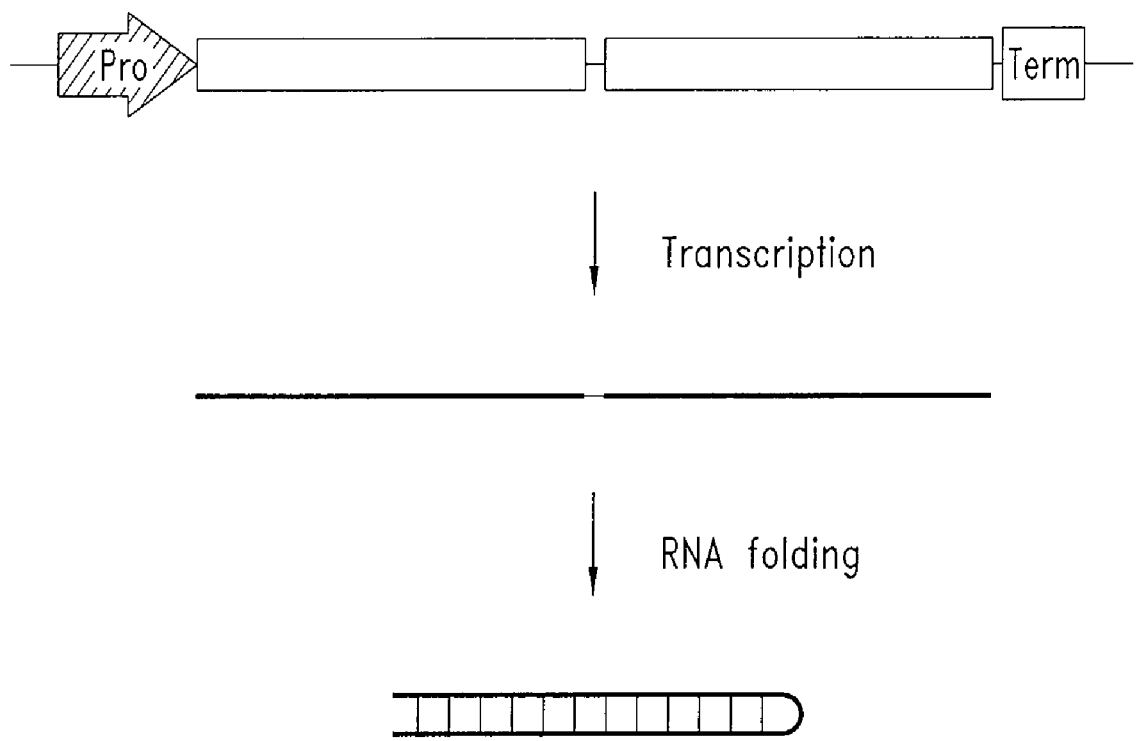
FIG. 1 is a schematic illustration of one class of dsRNA expression cassette that produces RNA with a hairpin.

Prior to setting forth the invention, it may be helpful to an understanding thereof to first set forth definitions of certain terms that will be used hereinafter.

"Expression cassette" refers to a transcription unit comprising a promoter operably linked to a nucleic acid molecule, such that transcription from the promoter results in synthesis of an RNA corresponding to the nucleic acid molecule. The expression cassette may further comprise a transcription termination and/or polyadenylation site.

"Isolated nucleic acid molecule" is a nucleic acid molecule that is not integrated in the genomic DNA of an organism or cell(s) derived from an organism. For example, a DNA molecule encoding a gene that has been separated from the genomic DNA of a eukaryotic cell is an isolated DNA molecule. Other examples of isolated nucleic acid molecules include chemically synthesized nucleic acid molecules, and nucleic acid molecules that have been made by recombinant means (e.g., PCR).

"Recombinant host" refers to any prokaryotic or eukaryotic cell that contains either a gene delivery vector or expression vector. This term also includes those prokaryotic or eukaryotic cells that have been genetically engineered to contain the cloned gene(s) in the chromosome or genome of the host cell.

An "antisense oligonucleotide" or "antisense molecule" refers to an oligonucleotide having a sequence (a) capable of forming a stable triplex with a portion of the gene, or (b) capable of forming a stable duplex with a portion of a mRNA transcript.

"Ribozyme" refers to a nucleic acid molecule that is capable of cleaving a specific ribonucleic acid sequence. Ribozymes may be composed of RNA, DNA, nucleic acid analogues (e.g., phosphorothioates), or any combination of these (e.g., DNA/RNA chimerics). Within particularly preferred embodiments, a ribozyme should be understood to refer to RNA molecules that contain antisense sequences for specific recognition, and an RNA-cleaving enzymatic activity.

"Ribozyme gene" refers to a nucleic acid molecule (e.g., DNA) consisting of the ribozyme sequence which, when transcribed into RNA, will yield the ribozyme.

"Promoter" is a nucleotide sequence that directs the transcription of a gene or non-protein encoding RNA. Typically, a promoter is located in the 5' region adjacent to the coding sequence of a gene or RNA to be expressed, and proximal to the transcription start site. If a promoter is an inducible promoter, then the level of transcription increases in response to an inducing agent.

"Gene delivery vector" or "GDV" is a vehicle for delivering nucleic acid sequences to cells. GDVs include viral vectors, nucleic acid vectors such as plasmids, naked nucleic acid molecules such as DNA or RNA, nucleic acid molecules complexed to one or more polycationic molecules capable of neutralizing part or all of the negative charge on a nucleic acid molecule and condensing the nucleic acid molecule into a compact structure, nucleic acid associated with liposomes, bacteria, and certain eukaryotic cells such as producer cells, capable of delivering a nucleic acid molecule having one or more desirable properties to host cells in an organism. As discussed below, the desirable properties include the ability to express a desired substance, such as a protein (e.g., an enzyme, antibody, antibody fragment, regulatory factor, ligand) or nucleic acid molecule (e.g., an antisense RNA, sense RNA, ribozyme), wherein the nucleic acid molecule carried by the GDV may itself be the active agent without requiring the expression of a desired substance. One example of a nucleic acid molecule is an antisense molecule that binds to mRNA and inhibits translation. Another example, is where the nucleic acid molecule encodes a ribozyme that binds and cleaves mRNA thereby inhibiting translation.

"Recombinant retroviral vector" refers to a gene delivery vector which is capable of directing the expression of a sequence(s) or gene(s) of interest. Preferably, the recombinant retroviral vector should include a 5' LTR, a tRNA binding site, a packaging signal, one or more heterologous sequences, an origin of second strand DNA synthesis and a 3' LTR. The recombinant retroviral vector also may include a transcriptional promoter/enhancer, or other elements which control gene expression by means such as alternate splicing, nuclear RNA export, post-translational modification of messenger, or post-transcriptional modification of protein. Optionally, the recombinant retroviral vector may also include selectable markers that confer, to transduced or transfected cells, resistance or sensitivity to one or more compounds.

The present invention relates to the introduction of nucleic acid sequences into a vertebrate to achieve expression of molecules (e.g., protein, RNA) that directly or indirectly stimulate one or more components of the immune response. The molecules may be expressed from any number of different delivery systems, either alone or co-expressed with an antigenic or therapeutic polypeptide.

Thus, the present invention can be utilized for a variety of therapeutic purposes, including for example, for the purpose of prophylactic and therapeutic vaccination, and for other gene therapy applications. In order to further an understanding of the inventions provided herein, a more detailed discussion is provided of (A) expression cassettes; (B) generation of gene delivery vectors; and (c) methods for utilizing expression cassettes and gene delivery vectors for a variety of applications (e.g., for therapeutic purpose, or, for use in laboratory setting).

A. Generation of Expression Cassettes

As noted above, the present invention provides a variety of expression cassettes that direct the generation of RNA, as well as optionally, a selected gene of interest, which increases, enhances, or stimulates an immune response. As described in more detail below, expression cassettes (comprising a promoter operably linked to a nucleic acid molecule of interest) can be generated to express double-stranded RNA, ribozymes and antisense RNA, as well as antigens or therapeutic polypeptides of interest. Each of these is discussed in more detail below.

Briefly, through use of the expression cassettes and/or gene delivery vectors described herein, double-stranded RNA (dsRNA) can be produced intracellularly for a variety of applications. The intracellular presence of dsRNA induces the synthesis of interferons $\alpha$, $\beta$, and $\gamma$ (IFN-$\alpha$, IFN-$\beta$, and IFN-$\gamma$; Type I interferon: IFN-$\alpha$ and IFN-$\beta$; Type II interferon: IFN-$\gamma$). Production of Type I and II interferons in turn induces both an antigen-specific and non-specific immune response, by directly stimulating CD8+ cytotoxic T lymphocytes (CTL), natural killer (NK) cells, and monocytes/macrophages. Furthermore these interferons enhance antigen presentation through increased expression of MHC class I and class II on the cell surface. Compositions and methods are provided herein for the expression of non-coding dsRNA in the context of expression of a desired antigen. Expression of dsRNA according to the invention enhances the overall robustness of antigen-specific immune responses.

Induction of Type I and II interferons, as a result of the intracellular presence of dsRNA in turn induces the synthesis of protein kinase R (PKR), and 2', 5 oligoadenylate synthetase (2',5' OAS) (Jacobs and Langland, *Virology* 219:339-349, 1996). Activation of PKR and 2', 5' OAS can in turn lead to apoptosis in a given cell, when the ratio of death agonists, for example Bax and Bak, to death antagonists, for example Bcl-2, exceeds unity (for reviews, see Kroemer, *Nat. Med.* 6:614-620, 1997; and Adams and Cory, *Science* 281:1322-1326, 1998). Activated PKR can directly effect this ratio through phosphorylation and inactivation of the translation factor eif-2$\alpha$ and I$\kappa$B. Phosphorylation of I$\kappa$B by PKR can lead to I$\kappa$B degradation and subsequent activation of NF-$\kappa$B (Maran, *Virology* 164:106-113, 1994). NF-$\kappa$B is a transcription factor that activates transcription of genes for inflammatory cytokines, including TNF$\alpha$ (Gilmore, *Cancer Biol.* 8:61-62, 1997). Induction of TNF$\alpha$ can induce apoptosis through the CrmA/P35-sensitive caspase-dependent pathway (Thornberry and Lazebnik, *Science* 281:1312-1316, 1998).

Induction of Type I and II interferons and apoptosis in the context of antigen expression enhances the specific immune response, through efficient priming of, for example, dendritic cells (DCs). As antigen presenting cells, DCs phagocytize apoptotic cells, and process antigens into peptides in the cytosol, which in turn bind to MHC class I or class II peptides, and are presented to T lymphocytes (Banchereau and Steinman, *Nature* 392:245-252, 1998). Induction of apoptosis, or the death pathway, in the context of antigen expression in order to enhance the immune response can be accomplished by a variety of different methods including, for example, expression of either caspase-dependent or caspase-independent genes, expression of death receptors (e.g., CD95 or TNFR1).

Figure 2:
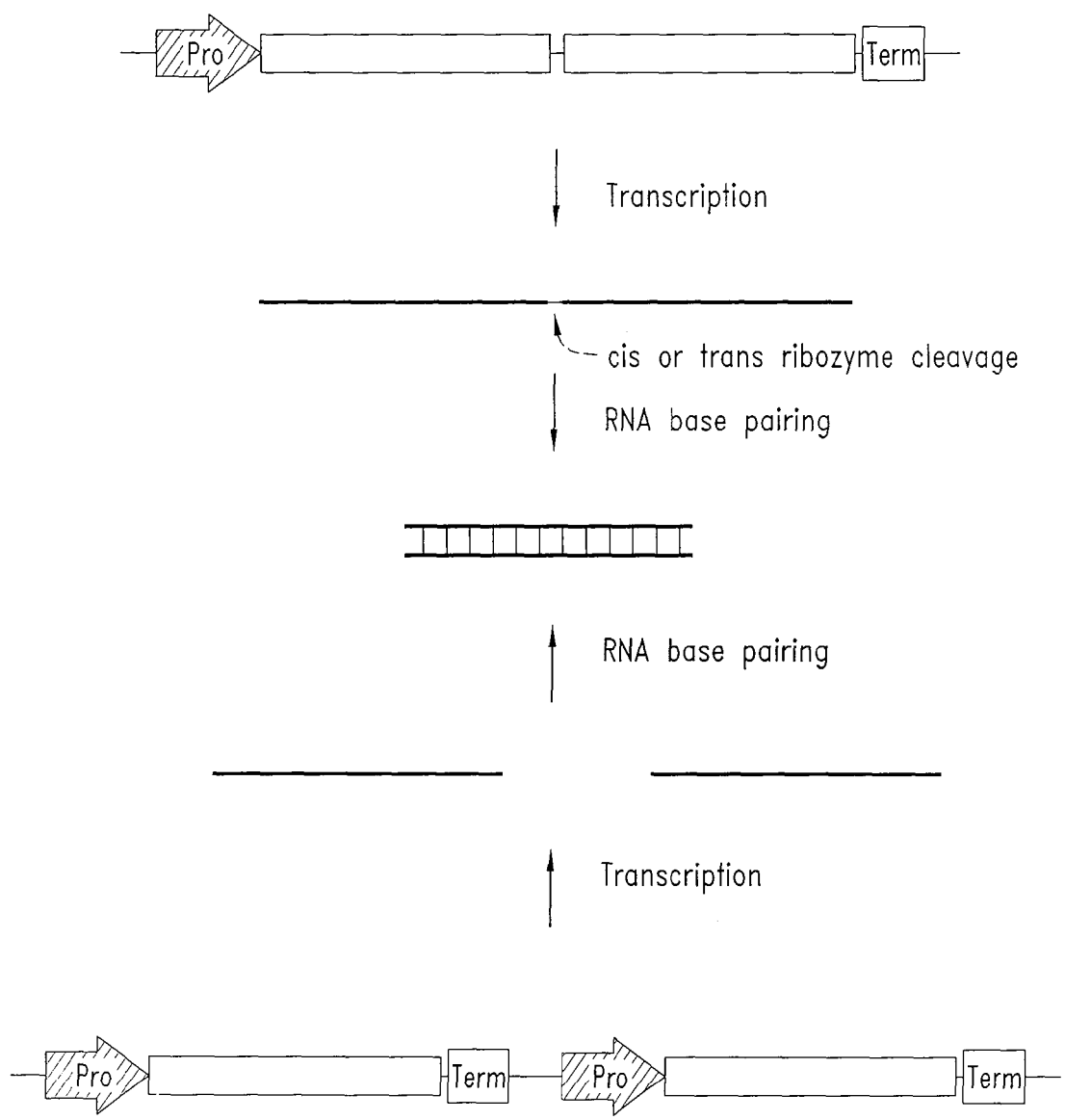
FIG. 2 is a schematic illustration of one class of dsRNA expression cassette that produces true double-stranded RNA.
Figure 3:
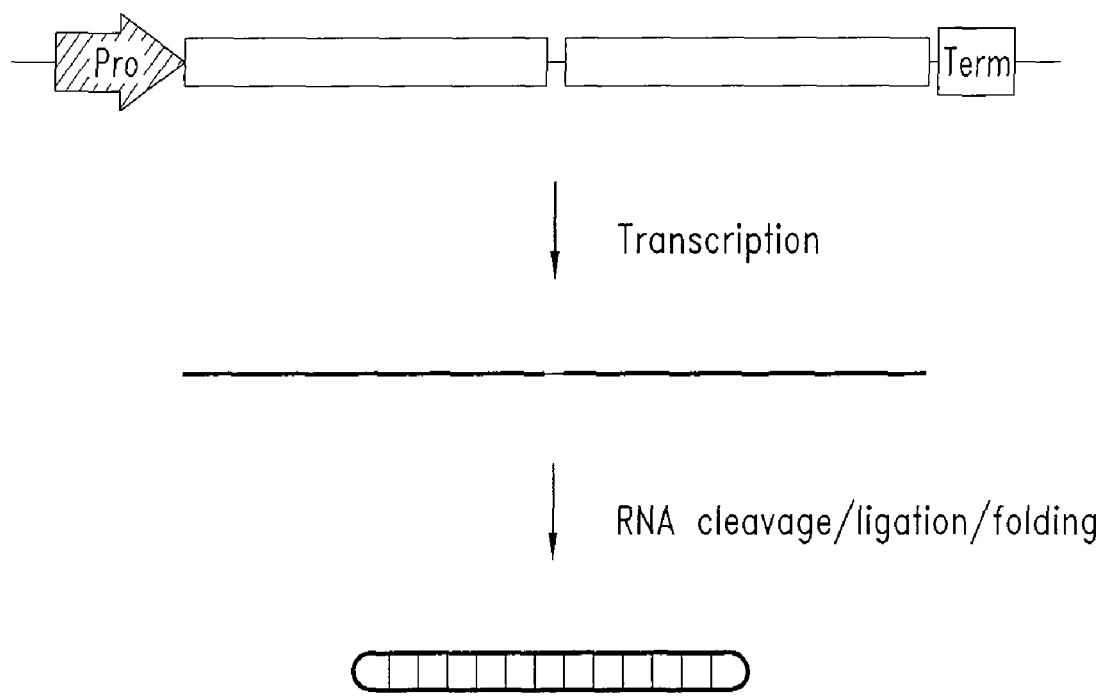
FIG. 3 is a schematic illustration of one class of dsRNA expression cassette that produces circular RNA.

Representative examples of suitable expression cassettes are described in more detail below, as well as in the figures (see FIGS. 1-3 for schematic illustrations of expression cassettes which create dsRNA through the use of hairpins (FIG. 1), true dsRNA (FIG. 2), and circular RNA (FIG. 3).

A wide variety of nucleic acid molecules may be expressed from the expression cassettes and/or gene delivery vectors of the present invention. Representative examples include (1) antisense RNA; (2) ribozymes; (3) polypeptides, including antigens and therapeutic proteins, and apoptotic polypeptides.

1. Antisense RNA

Within one embodiment of the invention delivery systems are provided which produce an antisense RNA sequence upon introduction into a host cell. Briefly, antisense RNA sequences are designed to bind to target RNA transcripts, and thereby prevent cellular synthesis of a particular protein or prevent use of that RNA sequence by the cell. In preferred embodiments, target RNA transcripts encode gene products that control or regulate various aspects of the immune response or apoptotic pathway.

Antisense sequences of the present invention may be of a variety of sizes, including for example 40, 60, 100, 250, 500, or even 1000 nucleotides. For preferred embodiments, the antisense sequence is less than 100 nucleotides. The antisense RNA sequence also may be 100% complementary to the target sequence, or may contain one or more "mismatches" that are not complementary provided that the antisense RNA maintains its ability to bind the target sequence under physiological conditions of the host.

Representative examples of such antisense sequences suitable for use within the present invention include antisense IRF2, YYK1, Cox2, IL-10, Bcl-2, Bcl-xL, and TGF-β. The antisense sequence may also be an antisense RNA complementary to RNA sequences necessary for pathogenicity. Alternatively, the biologically active nucleic acid molecule may be a sense RNA (or DNA) complementary to RNA sequences necessary for pathogenicity 2. Ribozymes Within other aspects of the present invention, delivery systems are provided which produce ribozymes upon introduction into a host cell. Briefly, ribozymes are RNA molecules used to cleave specific RNAs and are designed such that it can only affect one specific RNA sequence. Generally, the substrate binding sequence of a ribozyme typically is between 10 and 20 nucleotides long, although longer sequences also may be utilized. The length of this sequence is sufficient to allow hybridization with the target RNA and disassociation of the ribozyme from the cleaved RNA. Several different types of ribozymes may be constructed for use within the present invention, including for example, hammerhead ribozymes (Rossi, J. J. et al., *Pharmac. Ther.* 50:245-254, 1991) (Forster and Symons, *Cell* 48:211-220, 1987; Haseloff and Gerlach, *Nature* 328:596-600, 1988; Walbot and Bruening, *Nature* 334:196, 1988; Haseloff and Gerlach, *Nature* 334:585, 1988; Haseloff et al., U.S. Pat. No. 5,254,678), hairpin ribozymes (Hampel et al., *Nucl. Acids Res.* 18:299-304, 1990, and U.S. Pat. No. 5,254,678), hepatitis delta virus ribozymes (Perrotta and Been, *Biochem.* 31:16, 1992), Group I intron ribozymes (Cech et al., U.S. Pat. No. 4,987,071) and RNase P ribozymes (Takada et al., *Cell* 35:849, 1983); (see also, WO 95/29241, entitled "Ribozymes with Product Ejection by Strand Displacement"; and WO 95/31551, entitled "Novel Enzymatic RNA Molecules." (see also U.S. Pat. Nos. 5,116,742; 5,225, 337 and 5,246,921). Preferred ribozymes for use within the present invention include those which target RNA transcripts encoding gene products that control or regulate various aspects of the immune response or apoptotic pathway. Particularly preferred ribozymes are disclosed in more detail below.

3. Co-Expression of Antigens, Therapeutic Polypeptides, and Apoptotic Genes

In addition to the immunostimulatory RNAs of the present invention, a wide variety of genes encoding antigenic or therapeutic polypeptides also may be included in such delivery systems, either by co-expression from one vector or co-administration of separate vectors, including for example, sequences which encode palliatives such as lymphokines, toxins, or prodrugs, antigens which stimulate an immune response, and proteins which modulate the immune response or apoptotic pathway. Within various embodiments of the invention, the delivery systems provided herein may contain genes for two or more antigenic or therapeutic polypeptides.

a. Antigens

Within the present invention, constructs are provided which direct the expression of immunogenic portions of antigens from foreign organisms or other pathogenic agents (e.g., cancerous cells). Preferred vaccine antigens from foreign organisms are those that protect warm-blooded animals from diseases caused by infectious agents such as bacteria, fungi, parasites, and viruses.

Representative examples of such antigens particularly relevant for human vaccines include: viral antigens from arenaviruses such as lassa fever virus; rotavirus; adenovirus; human papillomavirus; retroviruses such as HIV, HTLV-I and -II; herpes viruses such as herpes simplex virus, Epstein-Barr virus, cytomegalovirus, varicella-zoster virus, and human herpes virus 6; picornaviruses such as poliovirus, human rhinovirus, and hepatitis A virus; togaviruses such as Venezuelan equine encephalitis, and rubella virus; hepatitis B virus; flaviviruses such as Dengue virus, tick-borne encephalitis virus, and hepatitis C virus; human coronavirus; rhabdoviruses such as rabies virus, and vesicular stomatitis virus; filoviruses such as ebola virus and marburg virus; paramyxoviruses such as human parainfluenza virus, mumps virus, respiratory syncytial virus, and measles virus; influenza virus; bunyaviruses such as hantaan virus, and Rift Valley fever virus; bacterial antigens (e.g., from *E. coli, streptococcus, staphylococcus,* mycobacteria; meningicoccus or *helicobacter*) fungal antigens and parasitic antigens (e.g. from *Leishmania* or malaria).

Representative examples of antigens particularly relevant for veterinary applications are derived from *Toxoplasma, Dirofilaria, Acanthocheilonema, Babesia, Brugia, Candida, Cryptococcus, Cryptosporidium, Dipetalonema, Eimeria, Encephalitozoon, Hepatozoon, Histoplasma, Isospora, Loa, Microsporidia, Neospora, Nosema, Onchocerca, Parafilaria, Plasmodium, Pneumocystis, Rochalimaea, Setaria, Stephanofilaria, Theileria, Toxoplasma,* and *Wuchereria,* viruses such as equine herpes virus, feline rhinotracheitis virus, porcine rotavirus, blue tongue virus, FIV, FeLV, BIV, EIAV, bovine papillomavirus, canine parvovirus, feline panleukopenia virus, foot-and-mouth disease virus, porcine enterovirus, TGEV, feline infectious peritonitis virus, bovine coronavirus, rabies virus, canine distemper virus.

As utilized within the context of the present invention, "immunogenic portion" refers to a portion of the respective antigen which is capable, under the appropriate conditions, of inducing an immune response (i.e., cell-mediated or humoral). "Portions" may be of variable size, but are preferably at least 9 amino acids long, and may include the entire antigen.

b. Therapeutic Polypeptides

Within one embodiment of the invention, expression cassettes and gene delivery vectors are provided which direct the expression of a gene product(s) that activates a compound with little or no cytotoxicity into a toxic product. Briefly, a wide variety of gene products which either directly or indirectly activate a compound with little or no cytotoxicity into a toxic product may be utilized within the context of the present invention. Representative examples of such gene products include HSVTK and VZVTK which selectively monophosphorylate certain purine arabinosides and substituted pyrimidine compounds, converting them to cytotoxic or cytostatic metabolites. More specifically, exposure of the drugs ganciclovir, acyclovir, or any of their analogues (e.g., FIAC, DHPG) to HSVTK, phosphorylates the drug into its corresponding active nucleotide triphosphate form.

Other therapeutic polypeptides that can be expressed from the cassettes and gene delivery vectors of the present invention include cytokines, such as IL-1, IL-2 (Karupiah et al., *J. Immunology* 144:290-298, 1990; Weber et al., *J. Exp. Med.* 166:1716-1733, 1987; Gansbacher et al., *J. Exp. Med.* 172: 1217-1224, 1990; U.S. Pat. No. 4,738,927), IL-3, IL-4 (Tepper et al., *Cell* 57:503-512, 1989; Golumbek et al., *Science* 254:713-716, 1991; U.S. Pat. No. 5,017,691), IL-5, IL-6 (Brakenhof et al., *J. Immunol.* 139:4116-4121, 1987; WO 90/06370), IL-7 (U.S. Pat. No. 4,965,195), IL-8, IL-9, IL-10, IL-11, IL-12, IL-13 (Cytokine Bulletin, Summer 1994), IL-14 and IL-15, particularly IL-2, IL-4, IL-6, IL-12, and IL-13, alpha interferon (Finter et al., *Drugs* 42(5):749-765, 1991; U.S. Pat. No. 4,892,743; U.S. Pat. No. 4,966,843; WO 85/02862; Nagata et al., *Nature* 284:316-320, 1980; Familletti et al., *Methods in Enz.* 78:387-394, 1981; Twu et al., *PNAS* 86:2046-2050, 1989; Faktor et al., *Oncogene* 5:867-872, 1990), beta interferon (Seif et al., *J. Virol.* 65:664-671, 1991), gamma interferons (Radford et al., *The American Society of Hepatology* 2008-2015, 1991; Watanabe et al., *PNAS* 86:9456-9460, 1989; Gansbacher et al., *Cancer Research* 50:7820-7825, 1990; Maio et al., *Can. Immunol. Immunother.* 30:34-42, 1989; U.S. Pat. No. 4,762,791; U.S. Pat. No. 4,727,138), G-CSF (U.S. Pat. Nos. 4,999,291 and 4,810,643), GM-CSF (WO 85/04188), tumor necrosis factors (TNFs) (Jayaraman et al., *J. Immunology* 144:942-951, 1990), CD3 (Krissanen et al., *Immunogenetics* 26:258-266, 1987), ICAM-1 (Altman et al., *Nature* 338:512-514, 1989; Simmons et al., *Nature* 331:624-627, 1988), ICAM-2, LFA-1, LFA-3 (Wallner et al., *J. Exp. Med.* 166(4):923-932, 1987), MHC class I molecules, MHC class II molecules, B7.1-0.3, $b_2$-microglobulin (Parnes et al., *PNAS* 78:2253-2257, 1981), chaperones such as calnexin, MHC linked transporter proteins or analogs thereof (Powis et al., *Nature* 354:528-531, 1991).

c. Apoptotic Genes

Apoptosis is the normal process of programmed cell death, which maintains tissue homeostasis (Kerr, J. F. et al., *Br. J. Cancer* 26:239-257, 1972). The process of apoptosis is regulated by signals generated when cytokines bind to their receptors, which in turn may either produce inductive or inhibitory signals that regulate the apoptotic process. Upon induction of apoptosis a cascade of zymogen activation occurs which eventually leads to the activation of endogenous nucleases that cleave chromatin between nucleosomes and reduce the content of intact DNA in apoptotic cells, thereby leading to cell death. While apoptosis is mediated by a variety of signals and complex interactions of cellular gene products, the results of these interactions ultimately feed into a cell death pathway that is, itself, a cascade of zymogen activation (i.e., proteolytic events) analogous to that of the blood coagulation cascade.

Several gene families and products that modulate the apoptotic process have now been identified. One such family is the Bcl-2 family, which includes cell death inhibitory proteins Bcl-2, Bcl-xL, and CED-9 as well as apoptotic promoting proteins, bax, bak, bcl-xS, and bad. Bcl-2 was the first recognized component of programmed cell death (Tsujimoto et al., *Science* 228:1440-1443, 1985; Nunez et al., *J. Immunol* 144: 3602-3610, 1990; Reed, *Nature* 387:773, 1997).

Briefly, Bcl-2 and its homologue Bcl-xL are death antagonists that associate mainly with the outer mitochondrial membrane, the endoplasmic reticulum, and nuclear envelope and moreover, have documented ion channel activity (Reed, *Nature* 387:773, 1997). These proteins may prevent apoptosis by regulating the electrical and osmotic homeostasis of the mitochondria, a process that is required to prevent mitochondrial swelling, outer membrane rupture, and subsequent cytochrome c release (Heiden et al., *Cell* 91:627-637, 1997). Release of cytochrome c from the mitochondria is believed to be the triggering event of the cell death cysteine protease cascade, through formation of the Apaf-1/caspase-9/cytochrome c complex (Li et al., *Cell* 91:479-489, 1997; Reed, *Cell* 91:559-562, 1997). This complex in combination with dATP in turn leads to the proteolytic activation of the caspase-9 zymogen thereby initiating the proteolytic cascade.

The cysteine proteases responsible for this cascade are aspartate-specific cysteine proteases and are collectively referred to as "caspase" proteins. The first member of the caspase family was identified as Interleukin-1β Converting Enzyme (ICE) which was found to be structurally and functionally related to the CED-3 protease that functions as a cell death effector in the roundworm *C. elegans* (Yuan et al., *Cell* 75:641, 1993). Following this discovery many other members of the ICE/CED-3 family were identified and include, for example, human ICE (interleukin-1-β converting enzyme) (caspase-1), ICH-1 (caspase-2), CPP32 (caspase-3), $ICE_{rel}II$ (caspase-4), $ICE_{rel}III$ (caspase-5), Mch2 (caspase-6), ICE-LAP3 (casepase-7), Mch5 (caspase-8), ICE-LAP6 (caspase-9), Mch4 (caspase-10), and others.

Given that the apoptotic process functions to maintain tissue homeostasis, a variety of pathological states can be associated with abnormal apoptotic regulation. Further, the loss or inhibition of apoptosis can lead to accumulation of virally infected cells or hyperproliferative cells such as tumor cells. Similarly, the inappropriate activation of apoptosis can also contribute to a variety of pathological disease states including, for example, ischemic injury. Accordingly, treatments which are specifically designed to modulate the apoptotic pathways in these and other pathological conditions can alter the natural progression of many of these diseases.

4. Obtaining a Desired Nucleic Acid Molecule of Interest

Sequences that encode the above-described antisense or ribozyme sequences, antigens, therapeutic polypeptides and apoptotic genes may be generated synthetically or recombinantly, or, obtained from a variety of sources, including for example, depositories such as the American Type Culture Collection (ATCC, Rockville, Md.). Isolated nucleic acid molecules encoding such antigens are readily generated by one of skill in the art using standard PCR methodologies, provided that at least some sequence data are available. Alternatively, cDNA sequences that encode the above-described antigens may be obtained from cells or cultures that express or contain the sequences. Briefly, within one embodiment, mRNA from a cell which expresses the gene of interest is reverse transcribed with reverse transcriptase using oligonucleotide dT or random primers. The single stranded cDNA may then be amplified by PCR (see U.S. Pat. Nos. 4,683,202; 4,683,195 and 4,800,159. See also *PCR Technology: Principles and Applications for DNA Amplification*, Erlich (ed.), Stockton Press, 1989) utilizing oligonucleotide primers complementary to sequences on either side of desired sequences. In particular, a double-stranded DNA is denatured by heating in the presence of heat stable Taq polymerase, sequence-specific DNA primers, dATP, dCTP, dGTP and dTTP. Double-stranded DNA is produced when synthesis is complete. This cycle may be repeated many times, resulting in a factorial amplification of the desired DNA.

Sequences encoding the above-described antigens also may be synthesized, for example, on an Applied Biosystems Inc. DNA synthesizer (Applied Biosystems, Foster City, Calif.).

B. Preparation of Gene Delivery Vectors

A wide variety of gene delivery vectors may be utilized to contain and express the expression cassettes described herein. The gene delivery vector may be of either viral or non-viral origin (see generally, Jolly, *Cancer Gene Therapy* 1:51-64, 1994; Kimura, *Human Gene Therapy* 5:845-852, 1994; Connelly, *Human Gene Therapy* 6:185-193, 1995; and Kaplitt, *Nature Genetics* 6:148-153, 1994; Donnelly et al., ibid). Gene therapy vehicles for delivery of constructs including a coding sequence of a therapeutic of the invention can be administered either locally or systemically (e.g., intravenously, intramuscularly, intradermally, subcutaneously, intratumorally, intranasally, orally, intrahepatically, intratracheally). These constructs can utilize viral or non-viral vector approaches as either an in vivo or ex vivo modality. Expression of such coding sequence can be induced using endogenous mammalian or heterologous promoters. Expression of the coding sequence in vivo can be either constitutive or regulated as is described in detail below.

Within one aspect of the present invention, the gene delivery vector is a plasmid-based vector. Representative examples of suitable vectors in this regard include those disclosed within U.S. Pat. No. 5,580,859 entitled "Delivery of Exogenous DNA Sequences in a Mammal," U.S. Pat. No. 5,589,466 entitled "Induction of a Protective Immune Response in a Mammal by Injecting a DNA Sequence," U.S. Pat. Nos. 5,688,688, 5,814,482 and 5,580,859, and Donnelly et al., ibid)

Within other aspects of the present invention, gene delivery vectors can be generated based upon a retrovirus. Briefly, retroviral gene delivery vectors of the present invention may be readily constructed from a wide variety of retroviruses, including for example, B, C, and D type retroviruses as well as spumaviruses and lentiviruses (see RNA Tumor Viruses, Second Edition, Cold Spring Harbor Laboratory, 1985). Such retroviruses may be readily obtained from depositories or collections such as the American Type Culture Collection ("ATCC"; Rockville, Md.), or isolated from known sources using commonly available techniques. Representative examples of retroviral gene delivery vectors are described in more detail in EP 0,415,731; PCT Publication Nos. WO 90/07936; WO 91/0285, WO 9311230; WO 9310218, WO 9403622; WO 9325698; WO 9325234; and U.S. Pat. Nos. 5,219,740, 5,716,613, 5,851,529, 5,591,624, 5,716,826, 5,716,832, and 5,817,491.

Other suitable gene delivery vectors can be generated from alphaviruses (see, e.g., U.S. Pat. Nos. 5,091,309 and 5,217,879, 5,843,723, and 5,789,245), recombinant adenoviral vectors (see, e.g., U.S. Pat. No. 5,872,005), and numerous other viruses such as pox viruses, such as canary pox virus or vaccinia virus (Fisher-Hoch et al., *PNAS* 86:317-321, 1989; Flexner et al., *Ann. N. Y. Acad. Sci.* 569:86-103, 1989; Flexner et al., *Vaccine* 8:17-21, 1990; U.S. Pat. Nos. 4,603,112, 4,769,330 and 5,017,487; WO 89/01973); adeno-associated vectors (see, e.g., U.S. Pat. No. 5,872,005); SV40 (Mulligan et al., *Nature* 277:108-114, 1979); herpes (Kit, *Adv. Exp. Med. Biol.* 215:219-236, 1989; U.S. Pat. No. 5,288,641); and lentivirus such as HIV (Poznansky, *J. Virol.* 65:532-536, 1991) or FIV.

C. Methods of Stimulating an Immune Response

The ability to recognize and defend against foreign pathogens is central to the function of the immune system. This system, through immune recognition, must be capable of distinguishing "self" from "non-self" (foreign), which is essential to ensure that defensive mechanisms are directed toward invading entities rather than against host tissues. The fundamental features of the immune system are the presence of highly polymorphic cell surface recognition structures (receptors) and effector mechanisms (antibodies and cytolytic cells) for the destruction of invading pathogens.

Cytolytic or cytotoxic T lymphocytes (CTL) are normally induced by the display of processed pathogen-specific peptides in conjunction with the MHC class I or class II cell surface proteins. Also stimulated by this type of antigen presentation are the generation and production antibodies, helper cells and memory cells. Within one embodiment of the present invention, presentation of immunogenic viral determinants in the context of appropriate MHC molecules efficiently induces optimal CTL responses without exposing the patient to the pathogen. This vector approach to immune stimulation provides a more effective means of inducing potent class I restricted protective and therapeutic CTL responses, because the type of immunity induced by the vector more closely resembles that induced by exposure to natural infection. Based on current knowledge of several viral systems, it is unlikely that exogenously supplied, non-replicating viral antigens, such as peptides and purified recombinant proteins, will provide sufficient stimulus to induce optimal class I-restricted CTL responses. Alternatively, vector-delivered expression of selected viral proteins or other antigens corresponding to a pathogenic condition, such as cancer, within target cells as described within the present invention provides such a stimulus.

By way of example, in the case of HIV-1 infections, patients develop antibodies specific for a variety of viral envelope-region determinants, some of which are capable of in vitro virus neutralization. Nevertheless, disease progression continues and the patients eventually succumb to the disease. Low-level CTL responses against infected patients' cells (Plata et al., *Nature* 328:348-351, 1987) and against target cells infected with recombinant vaccinia vectors expressing HIV gag, pol, or env (Walker et al., *Nature* 328: 345-348, 1987; Walker et al., *Science* 240:64-66, 1988) have been detected in some HIV-1 seropositive patients. In addition, it has recently been shown that murine as well as human CTL can be induced by autologous stimulator cells expressing HIV gp120 via transfection (Langlade-Demoyan et al., *J. Immunol.* 141:1949, 1988). Improved CTL induction could be therapeutically advantageous to infected patients and provide effective preventive therapy to individuals under noninfectious conditions. HIV infection itself may not be producing an adequate CTL response because other elements associated with HIV infection may prevent proper immune stimulation. In addition, it may be that stimulation of T-cells by infected cells is an interaction that leads to infection of the stimulated T-cells.

HIV is only one example. This approach can be effective against many virally linked diseases or cancers where a characteristic antigen (which does not need to be a membrane protein) is expressed, such as in HPV and cervical carcinoma, HTLV-I-induced leukemia's, prostate-specific antigen (PSA) and prostate cancer, mutated p53 and colon carcinoma, GD2 antigen and melanoma.

1. In Vivo Administration

Within certain aspects of the present invention, methods are provided for delivering one or more nucleotide sequences to a warm-blooded animal, comprising the step of administering to the warm-blooded animal a gene delivery vector, such as plasmid DNA, retrovirus vector, adenovirus vector, AAV vector, poxvirus vector, herpesvirus vector, alphavirus vector, and eukaryotic layered vector initiation system, expressing the nucleotide sequence as described above.

Gene delivery vectors may be administered to warm-blooded animals either directly (e.g., intravenously, intramuscularly, intraperitoneally, subcutaneously, orally, rectally, intraocularly, intranasally, intradermally, intratumorally), or by various physical methods such as lipofection (Felgner et al., *Proc. Natl. Acad. Sci. USA* 84:7413-7417, 1989), direct DNA injection (Acsadi et al., *Nature* 352:815-818, 1991); microprojectile bombardment (Williams et al., *PNAS* 88:2726-2730, 1991); liposomes of several types (see, e.g., Wang et al., *PNAS* 84:7851-7855, 1987); $CaPO_4$ (Dubensky et al., *PNAS* 81:7529-7533, 1984); DNA ligand (Wu et al, *J. of Biol. Chem.* 264:16985-16987, 1989); administration of nucleic acids alone (WO 90/11092); or administration of DNA linked to killed adenovirus (Curiel et al., *Hum. Gene Ther.* 3:147-154, 1992); via polycation compounds such as polylysine, utilizing receptor specific ligands; as well as with psoralen inactivated viruses such as Sendai or Adenovirus. In addition, the eukaryotic layered vector initiation systems may either be administered directly (i.e., in vivo), or to cells which have been removed (ex vivo), and subsequently returned.

Within one embodiment of the invention, the expression cassette or gene delivery vector is delivered (either in vivo or ex vivo) to dendritic cells (DC). Briefly, dendritic cells (DC) are professional antigen presenting cells, which initiate and modulate the immune response. In particular, DCs are potent stimulators of B and T lymphocytes (for review, see Banchereau and Steinman, *Nature* 392:245-252, 1998). Stimulation of the T and B lymphocyte antigen-specific effectors occurs by presentation by the dendritic antigen presentation cells, in which processed antigen is displayed in conjunction with major histocompatibility complex (MHC) molecules of two alternative types (MHC class I, or MHC class II), to T lymphocytes, via the T-cell antigen receptor. Antigen presentation via MHC class I results in a cellular CD8+ cell (cytotoxic T cell, CTL) response, whereas antigen presentation via MHC class II results in stimulation of CD4+ cells, and subsequently B lymphocytes, resulting in a humoral (antibody, Ab) response.

The present invention relates broadly to compositions and methods for stimulating the immune response through the utilization of various RNA and other molecules synthesized in vivo from an expression cassette contained within an appropriate gene delivery vehicle. As will become evident from the detailed examples below, such immunostimulatory RNA molecules may comprise sequences which form double-stranded (ds) RNA structures within a desired cell, either by base-pairing with RNAs already present in the cell or via self-complementing sequences within the expressed RNA molecule. The presence of such dsRNA molecules within a cell typically will lead to the induction of one or more elements of the immune system, including interferon responses. Further, the immunostimulatory RNA molecules of the present invention also may comprise antisense or ribozyme sequences that specifically target one or more cellular gene products, such that suppression or down-regulation of the targeted gene product results in the up-regulation and increased expression of a second gene product associated with an immune response. The RNA molecules of the present invention may be expressed alone or co-expressed with one or more antigens derived from a pathogenic agent (e.g., infectious agent, cancer), and are suitable for use in a wide variety of gene delivery systems, such as plasmid DNA, retrovirus vectors, adenovirus vectors, AAV vectors, poxvirus vectors, herpesvirus vectors, and alphavirus vectors.

The following examples are offered by way of illustration, and not by way of limitation.

EXAMPLES

Example 1

Construction of Gene Delivery Vectors that Synthesize Double-Stranded RNA in Transfected Cells The construction of gene delivery vectors that provide an enhanced immune response to a desired antigen when inoculated into a warm-blooded animal is described below. As an example, plasmids that express only non-protein encoding double-stranded RNA, or in addition, which also express a desired antigen from a pathogenic agent, are illustrated.

A. Expression Cassettes that Transcribe Noncoding dsRNA in Transfected Cells

In the present invention, constructions of expression cassettes that transcribe non-coding dsRNA in desired transfected target cells in vivo are provided (see FIGS. 1-3). As a preferred example, synthesis of dsRNA is from an RNA polymerase III promoter-based expression cassette. However, other promoters (e.g., RNA polymerase I and II) may be readily substituted. Thus, in cells transfected in vivo with the plasmid DNA constructs described herein, significant levels of non protein-encoding dsRNA are synthesized either alone, or in addition to a specific desired antigen from a pathogenic agent. Expression of the dsRNA results in an overall enhanced immune response to the antigen.

Figure 4:
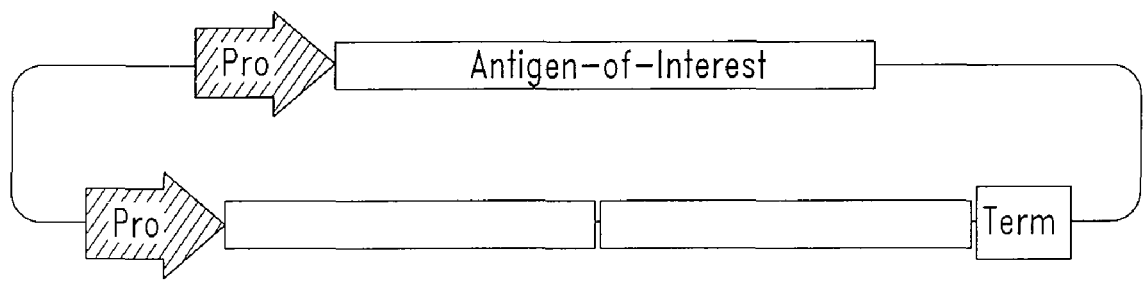
FIG. 4 is a schematic illustration of DNA vectors with double-stranded RNA and antigen cassettes.

Specifically, an RNA polymerase III (pol III) promoter-based non-coding dsRNA expression cassette (FIG. 1) was constructed to contain the following ordered elements: Adenovirus 2 VA1 RNA promoter (nucleotides −70/+30), nucleotides 447-547 of the Rhinovirus 1A 3C protease gene, in which the A nucleotide present in an ATG codon present in any alternative reading frame was changed, a 10 nucleotide-long stretch of C residues, nucleotides 447-547 of the Rhinovirus 1A 3C protease gene, in an antisense orientation, and the RNA polymerase III consensus transcription termination sequence. Additionally, plasmids were constructed which additionally contained an RNA polymerase II (pol II) expression cassette expressing an antigen (FIG. 4), consisting of the following ordered elements: CMV promoter, intron, heterologous gene (lac Z or the glycoprotein B gene from herpes simplex virus type 1, and the SV40 polyadenylation/transcription termination sequence. Plasmids were constructed in which the RNA products transcribed from the pol II and pol III expression cassettes were in the same or in opposite directions, relative to each other. These ordered elements in the pol II and pol III expression cassettes described above were cloned into a pUC-derived kanamycin-resistant plasmid DNA vector for propagation in E. coli, as outlined below, using standard recombinant DNA techniques (Maniatis and Sambrook). The plasmids were constructed on the pBGS131 (Spratt et. al., Gene 41:337-342, 1986; ATCC #37443) vector backbone that was modified to remove extraneous sequences, to insert an alternate multiple-cloning site (PmeI-BglII-XhoI-NotI-EcoRI-PmeI), and to render an existing XhoI site within the kanamycin resistance gene non-functional. This modified vector known as pBGSVG and has been described previously (WO 97/38087).

For expression of genes encoding desired antigens, the RNA polymerase II cassette from the pCI vector (Promega, Madison, Wis.) was inserted into the pBGSVG plasmid vector, described above. The pCI vector DNA was digested first with BamHI and the 5'-overhang ends were filled in by incubation with the Klenow enzyme and dNTPs. Following purification with GeneCleanII (Bio 101, Vista, Calif.), the treated plasmid DNA was then digested with BglII and the 1348 bp fragment, consisting, in order, of the human cytomegalovirus (CMV) immediate early enhancer/promoter, a chimeric intron composed of the 5'-splice site for the β-globin intron and the 3'-splice site from an IgG intron, a multiple cloning site, and the SV40 late region poly(A) sequence, was inserted into the pBGSVG plasmid digested with Eco RI, fill-in of 5'-overhang ends, and digested with BglII. Gel purification of the pol II expression cassette-containing fragment was not necessary, as clones were selected with kanamycin-containing media on which bacteria containing the pBGSVG (kan$^r$ gene) vector, but not the pCI (amp$^r$ gene) vector, can grow. This plasmid was designated pBGSVG-pol II.

The lac Z gene or the glycoprotein B (gB) gene from HSV-1 was then inserted into the polylinker of pBGSVG-pol II. The source of the lac Z gene was the pSV-β-Galactosidase Control Vector (Promega, Madison, Wis.), from which it was isolated as a HindIII-BamHI 3737 bp fragment, ligated into the pKS+ plasmid (Stratagene, La Jolla, Calif.), then re-isolated by digestion with XhoI and NotI, and ligated into the pBGSVG-pol II plasmid that was digested with XhoI and NotI. This plasmid was designated pBGSVG-pol II/β-gal.

The HSV-1 KOS strain glycoprotein B (gB) gene was obtained from Dr. Martin Muggeridge (LSU Medical Center, Shreveport, La.) and subcloned into the pBGSVG-pol II plasmid between the XhoI and XbaI sites within the multiple cloning sequence. This plasmid was designated pBGSVG-pol II/gB-1.

The pol III-based expression cassette was then inserted into the pBGSVG, pBGSVG-pol II/β-gal, or pBGSVG-pol II/gB-1 plasmids, at the unique BglII site. Assembly of the desired components in the pol III-based expression cassette was performed by PCR to juxtapose the following ordered sequences:

```
Ad2 Stuffer (nts. 1051-10584; SEQ ID NO: 5):
5'CCATGGTCGGGACGCTCTGGCCGGTGAGGCGTGCGCAGTCGTTGACGC

TCTGGA-3'

Ad2 VA1RNA promoter [(-70/+30) (nts. 10585-10682);
SEQ ID NO: 6]:
5'CCGTGCAAAAGGAGAGCCTGTAAGCGGGCACTCTTCCGTGGTCTGGTG

GATAAATTCGCAAGGGTATCATGGCGGACGACCGGGGTTCGAACCCCGG

A-3'

Rhinovirus 1A 3C Protease (nts. 447-457)
SEQ ID NO: 7):
5'CCTAAAACCAAAGTACCTGAAAGAAGAGTAGTTGCTCAAGGTCCAGAA

GAAGAATTTGGAAGGTCAATTCTCAAAAACAATACTTGTGTGATTACTAC

AGG-3'

Stem (SEQ ID NO: 8):
5'-CCCCCCCCCC-3'

Rhinovirus 1A 3C Protease (nts. 447-457) ANTISENSE
(SEQ ID NO: 9):
5'CCTGTAGTAATCACACAAGTATTGTTTTTGAGAATTGACCTTCCAAAT

TCTTCTTCTGGACCTTGAGCAACTACTCTTCTTTCAGGTACTTTGGTTTT

AGG-3'

RNA polymerase III termination sequence
(SEQ ID NO: 10):
5'-GCGCTTTTTGCGC-3'
```

Additionally, the following restriction sites were interspersed within the pol III expression cassette in order to facilitate interchanging the ordered elements present within the construct:

| Enzyme: | Recognition Sequence: |
|---------|----------------------|
| BglII   | A'GATCT              |
| BspEI   | T'CCGGA              |
| EcoRI   | G'AATTC              |
| XbaI    | T'CTAGA              |

The configuration of the ordered sequence elements present in the pol III expression cassette is 5'-BglII-Ad2 Stuffer-Ad2 VA1 promoter-XbaI-Rhinovirus Sense Stem-Loop-Rhinovirus Antisense Stem-EcoRI-pol III termination-BspEI-BglII-3'

Juxtaposition of the sequence elements shown above to construct the pol III-based expression cassette was accomplished in two steps. The first step used the partially complementary oligonucleotides shown below, each at 1 μM concentration in a short (10 cycle) PCR amplification:

```
Ad2VA 1F (SEQ ID NO: 11):
5'AGATCTCCATGGTCGGGACGCTCTGGCCGGTGAGGCGTGCGCAGTCGT

TGACGCTCTGGACCGTGCAAAAGGAGAGCC-3'

Ad2VA 1R (SEQ ID NO: 12):
5'CCCTTGCGAATTTATCCACCAGACCACGGAAGAGTGCCCGCTTACAGG

CTCTCCTTTT-3'

Ad2VA 2F (SEQ ID NO: 13):
5'AATTCGCAAGGGTATCATGGCGGACGACCGGGGTTCGAACCCCGGATC

TAGACCTAAAACCAAAGTACCTGAAAGAAGA-3'

Ad2VA 2R (SEQ ID NO: 14):
5'TGAGAATTGACCTTCCAAATTCTTCTTCTGGACCTTGAGCAACTACTC

TTCTTTCAGG-3'
```

-continued

Ad2VA 3F (SEQ ID NO: 15):
5'GGTCAATTCTCAAAAACAATACTTGTGTGATTACTACAGGCCCCCCC

CCCCTGTAGTAATCACACAAGTATTGTTTTT-3'

Ad2VA 3R (SEQ ID NO: 16):
5'AGTAGTTGCTCAAGGTCCAGAAGAAGAATTTGGAAGGTCAATTCTCAA

AAACAATACT-3'

Ad2VA 4F (SEQ ID NO: 17):
5'TGAGCAACTACTCTTCTTTCAGGTACTTTGGTTTTAGGGAATTCGCGC

TTTTTGCGCTCCGGAAGATCT-3'

Ad2VA 4R (SEQ ID NO: 18):
5'-AGATCTTCCGGAGCGCAAAAAG-3'

PCR amplification of the oligonucleotides comprising the pol III-based expression cassette shown above was performed in a single reaction, using the Vent$_R$ DNA polymerase (New England Biolabs, Beverly, Mass.), and reaction conditions as suggested by the supplier, containing in addition 2 mM MgSO$_4$, 5% DMSO, and Hot Start Wax beads (Perkin-Elmer), with the PCR amplification protocol, as shown below.

| Temperature (° C.) | Time (Min.) | No. Cycles |
|---|---|---|
| 95 | 2 | 1 |
| 95 | 0.5 | |
| 55 | 0.5 | 10 |
| 72 | 0.5 | |

The PCR products were purified (QIAquick PCR purification kit, QIAGEN, Chatsworth, Calif.) and the purified reaction products were used in a second PCR amplification, with the primer pair shown below:

```
Ad2 PCR 1F (SEQ ID NO: 19):
5'-CCCTTCCCAGATCTCCATGGTCGGGACG-3'

Ad2 PCR 1R (SEQ ID NO: 20):
5'-TTTCCTTTAGATCTTCCGGAGCGCAAAAAG-3'
```

PCR amplification of the pol III-based expression cassette from the first PCR amplification shown above was performed with the Vent$_R$ DNA polymerase (New England Biolabs, Beverly, Mass.), and reaction conditions as suggested by the supplier, containing in addition 2 mM MgSO$_4$, 5% DMSO, and Hot Start Wax beads (Perkin-Elmer), with the PCR amplification protocol shown below.

| Temperature (° C.) | Time (Min.) | No. Cycles |
|---|---|---|
| 95 | 2 | 1 |
| 95 | 0.5 | |
| 55 | 0.5 | 20 |
| 72 | 0.5 | |
| 72 | | 1 |

The products of this second PCR reaction were purified with a QIAquick kit, and then inserted directly into the pCR Blunt plasmid DNA vector (Invitrogen, Carlsbad, Calif.). This plasmid was designated pCR-pol III.

Alternatively, the purified products of this second PCR reaction were digested with BglII, purified, and ligated into the pBGSVG, pBGSVG-pol II/β-gal, or pBGSVG-pol II/gB-1 plasmids, prepared by digestion with BglII, treatment with calf intestinal alkaline phosphatase, and purification. With all plasmid constructs, clones containing the pol III expression cassette in both orientations (F or R, below) were isolated. These plasmids were designated:
  pBGSVG-pol III(F)
  pBGSVG-pol III(R)
  pBGSVG-pol II/β-gal-pol III(F)
  pBGSVG-pol II/β-gal-pol III(R)
  pBGSVG-pol II/gB-1-pol III(F)
  pBGSVG-pol II/gB-1-pol III(R)

To demonstrate functionality of the pol III expression cassette, cultured cells were transfected with pBGSVG-pol II/β-gal-pol III(F), pBGSVG-pol II/β-gal-pol III(R), or pBGSVG-pol II/β-gal plasmid, and expression of the predicted double-stranded RNA species was determined by RNA dot blot analysis of total RNA purified at 48 hr post-transfection, and treated subsequently with DNase. The predicted sequence of double-stranded (i.e., complementary) RNA, by virtue of its structure, should also be resistant to treatment with RNase. Baby hamster kidney-21 (BHK-21) cells were transfected with 1.0 µg of plasmid DNAs complexed with 4.0 µl of a commercially available lipid (Lipofectamine, GIBCO-BRL). Eagle minimal essential medium supplemented with 10% fetal bovine sera was added to the cells at 4 hours post transfection (hpt), unless otherwise indicated. Transfected cells were incubated at 37° C. At 48 hrs post transfection, β-galactosidase reporter gene expression was determined by direct in situ staining of fixed cells with X-gal as described previously (MacGregor, *Cell Mol. Genet.* 13:253-265, 1987). The efficiency of transfection with each of the three test plasmids was equivalent and approximately 10%. Alternatively in other samples, total RNA was isolated using a commercially available reagent (Tel-Test, TX), according to the instructions of the supplier. All samples were treated with DNase. Half of the samples also were treated with RNase, to lower the viscosity of the sample and to demonstrate the presence of a double-stranded RNA species, resistant to nuclease digestion. The purified samples were loaded onto Zeta Probe (Bio-Rad, Richmond Calif.), as follows, and hybridized with $^{32}$P-labeled Ad2VA 3R probe. The dsRNA was found to be expressed in cells transfected with the pBGSVG-pol II/β-gal-pol III(F) and pBGSVG-pol II/β-gal-pol III(R) plasmids, but not pBGSVG-pol II/β-gal plasmid, demonstrating that as expected, the pol III-based expression cassettes synthesize a double-stranded RNA species that is resistant to RNase.

In addition to the dsRNA configuration described above, a number of dsRNA cassette variations or modifications are readily made by one of skill in the art. These include alternative sequences which form a similar dsRNA hairpin, but with the same or other sequences that form a longer or shorter region of dsRNA, nucleotide substitution(s) resulting in less than 100% base-pairing within the dsRNA structure, insertion of a ribozyme sequence within the non-base paired loop region for cleavage into two separate, complementary RNAs which form dsRNA (FIG. 2), sequences which form circular, self-complementary "viroid-like" dsRNA (FIG. 3), and the use of two separate expression cassettes for transcription of complementary RNAs which form dsRNA (FIG. 2).

Example 2

Immune Stimulation by Promotion of Apoptosis

Figure 5A:
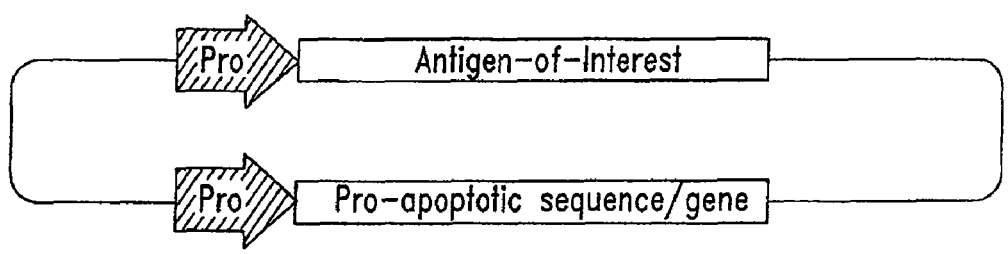
FIGS. 5A and 5B are schematic illustrations of plasmid vectors with pro-apoptotic and antigen cassettes.
Figure 5B:
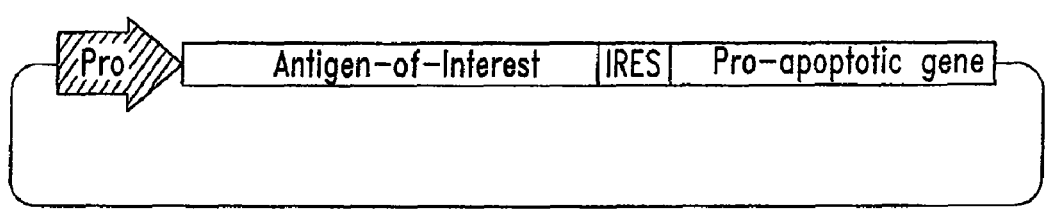

The present invention also provides compositions and methods for stimulation of an immune response specific for a pathogenic agent by expressing, in addition to an antigen from the pathogenic agent, one or more nucleic acid sequences that promote apoptosis. The expressed nucleic acid sequence that promotes apoptosis may be coding (e.g., encode a polypeptide) or non-coding (e.g., ribozyme, antisense RNA); and, the promotion of apoptosis may be direct (e.g., via an inductive signal) or indirect (e.g., suppression of an anti-apoptotic gene). Furthermore, expression cassettes containing the nucleic acid sequences that promote apoptosis may be part of the same gene delivery vehicle that expresses the antigen (FIG. 5), as distinct cassettes or a single cassette (i.e., using an IRES), or may be contained within a different gene delivery vehicle from that which expresses the antigen. In those instances where the pro-apoptotic sequence is expressed from a different gene delivery vehicle than the antigen expressing gene delivery vehicle, administration to a warm-blooded animal may be simultaneous, or separately in any desired order.

Numerous elements of the apoptotic regulatory cascade may be selected for use in accordance with the teachings of the present invention, including for example, the expression of pro-apoptotic gene products such as Bax, Bak, Bok, Bik, Blk, Hrk, BNIP3, BimL, Bad, Bid, Fas ligand and EGL-1, or the suppression of anti-apoptotic gene products such as Bcl-2, Bcl-xL and CED-9. In addition, it should be appreciated by those of skill in the art that although vector constructions are illustrated with only one antigen, this antigen is provided as an example and based on the teachings provided herein, alternative antigens may be chosen from a variety of pathogenic agents, including for example, viruses, bacteria, fungi, parasites, and cancer cells, provided that sufficient sequence data is available to facilitate the cloning of the antigens.

A. Co-Expression of a Proapoptotic Gene Product

To demonstrate the immunostimulatory effects of expressing both a pro-apoptotic sequence and vaccine antigen from a single gene delivery vector, herpes simplex virus type 1 (HSV-1) glycoprotein B, for example, was chosen as the antigen and murine BAXα, for example, was chosen as the pro-apoptotic gene product. Glycoprotein B provides a well-characterized measure of both humoral and cellular immune induction, as well as protection from virulent HSV challenge in a mouse model (Hariharan et al., *J. Virol.* 72:950-958, 1998). Murine BAXα is preferred over human BAXα for vaccine studies in the mouse model; however, details also are provided for similar constructs containing human BAXα. Construction of a plasmid DNA vector expressing both HSV-1 glycoprotein B and BAXα is accomplished by first isolating a fragment comprising the ordered elements CMV immediate early promoter, HSV-1 glycoprotein B, SV40 polyadenylation signal from plasmid pCI-gB (Hariharan et al., ibid). Plasmid pCI-gB is digested with BglII and BamHI, the DNA is blunt-ended using Klenow enzyme and dNTPs, the glycoprotein B containing fragment is purified from an agarose gel using GeneCleanII (BIO101, Vista, Calif.), and then ligated into a previously described plasmid vector pBGSVG (WO 97/38087) digested with PacI and also blunt-ended, using T4 DNA polymerase and dNTPs. The resulting construct is designated pBGSV-gB.

Insertion of an expression cassette for BAXα into pBGSV-gB is accomplished by first isolating from plasmid pCI (Promega, Madison, Wis.), a fragment comprising the ordered elements CMV immediate early promoter, multiple cloning site, SV40 polyadenylation signal. The fragment is isolated by digestion with BglII and BamHI, blunt-ending with Klenow and dNTPs, and purification from an agarose gel using GeneCleanII. The fragment then is ligated into plasmid pBGSV-gB that has been digested with PmeI, treated with alkaline phosphatase, and purified from an agarose gel, to produce the construct pBGSV-gB-cass2. BAXα is obtained by PCR amplification using two oligonucleotide primers:

```
BAXαfwd
                                (SEQ ID NO: 21)
5'ATATATGAATTCGGTGATGGACGGGTCCGGGGAGCAG BAXarev
                                (SEQ ID NO: 22)
5'TATATAGAATTCTCAGCCCATCTTCTTCCAGATGGTG
``` that contain flanking EcoRI restriction sites, PFU Turbo polymerase (Stratagene, San Diego, Calif.) according to the manufacturer's instructions, and template DNA from mouse or human B cell cDNA libraries (CLONTECH, Palo Alto, Calif.) or from commercially available plasmids (INVIVOGEN, San Diego, Calif.). Alternatively, polyA purified RNA from mouse and human lymphoid cells (e.g., cell lines RL7 and FL5.12; Oltvai et al., *Cell* 74:609-619, 1993) may be used as template for reverse transcriptase coupled PCR reactions. Following amplification, the PCR product is purified with a QIAquick kit (QIAGEN, Chatsworth, Calif.), digested with EcoRI, re-purified with QIAquick, and ligated with plasmid pBGSV-gB-cass2 that also has been digested with EcoRI and treated with alkaline phosphatase. Constructs are obtained with the BAXα insert in both the correct and opposite (negative control) orientation, and these plasmids are referred to as pBGSV-gB-BAX and pBGSV-gB-BAXrev.

Similar constructions that express other pro-apoptotic genes or antigens, are readily constructed from these teachings by one of skill in the art.

B. Co-Expression of Antisense RNA Specific for Anti-Apoptotic Genes

In alternative constructs, an antisense or ribozyme sequence, which specifically hybridizes to the mRNA of an anti-apoptotic gene, is expressed from a cassette, such as an RNA polymerase III (pol III) cassette. As described above, this cassette preferably is constructed as part of the same gene delivery vector (e.g., plasmid DNA) which expresses the desired antigen. However, it may also be contained within a separate vector that is administered to the same vaccinee as the antigen expressing gene delivery vector.

For example, an cassette is constructed wherein an RNA polymerase III promoter is operably linked with a sequence which, when transcribed, gives rise to an antisense RNA that specifically binds to the 5' region of the anti-apoptotic Bcl-2 gene mRNA (Tsujimoto and Croce, *Proc. Natl. Acad. Sci. USA* 83:5214-5218, 1986). Specifically, a cassette comprising the following ordered elements: EcoRI restriction site for cloning, Adenovirus 2 VA1 RNA promoter (nucleotides −70/+30), nucleotides 4-44 of the human Bcl-2 gene coding sequence, RNA polymerase III consensus transcription termination sequence, and EcoRI restriction site for cloning. Additional or alternative Bcl-2 sequences also may be substituted for nucleotides 4-44. In order to provide a mechanism for demonstrating the immunostimulatory effect of this approach, the elements are inserted into the previously described pBGSV-gB construct, which encodes glycoprotein B of HSV.

Assembly of the desired components in the pol III-based expression cassette is performed by PCR to juxtapose the following ordered sequences:

```
Ad2 Stuffer (nts. 1051-10584; SEQ ID NO: 23):
5'CCATGGTCGGGACGCTCTGGCCGGTGAGGCGTGCGCAGTCGTTGACGC
TCTGGA-3'
```

-continued

Ad2 VA1RNA promoter [(-70/+30) (nts. 10585-10682; SEQ ID NO: 24)]:
5'CCGTGCAAAAGGAGAGCCTGTAAGCGGGCACTCTTCCGTGGTCTGGTG

GATAAATTCGCAAGGGTATCATGGCGGACGACCGGGGTTCGAACCCCG

GA-3'

Human Bcl-2 coding sequence comprising nucleotides 4-44 (SEQ ID NO: 25)
5'GCGCACGCTGGGAGAACGGGGTACGACAACCGGGAGATAGT RNA polymerase III termination sequence (SEQ ID NO: 26):
5'-GCGCTTTTTGCGC-3'

Juxtaposition of the sequence elements shown above to construct the pol III-based expression cassette is accomplished in two steps. The first step uses the partially complementary oligonucleotides shown below, each at 1 µM concentration in a short (10 cycle) PCR amplification:

Ad2VAbcl 1F (SEQ ID NO: 27):
5'GAATTCCATGGTCGGGACGCTCTGGCCGGTGAGGCGTGCGCAGTCGTT

GACGCTCTGGACCGTGCAAAAGGAGAGCC-3'

Ad2VAbcl 1R (SEQ ID NO: 28):
5'CCCTTGCGAATTTATCCACCAGACCACGGAAGAGTGCCCGCTTACAGG

CTCTCCTTTT-3'

Ad2VAbcl 2F (SEQ ID NO: 29):
5'AATTCGCAAGGGTATCATGGCGGACGACCGGGGTTCGAACCCCGGAAC

TATCTCCCGGTTGTCGTACCCCGTTC-3'

Ad2VAbcl 2R (SEQ ID NO: 30):
5'GAATTCGCGCAAAAAGCGCGCGCACGCTGGGAGAACGGGGTACGA-3'

PCR amplification of the oligonucleotides comprising the pol III-based expression cassette shown above is performed in a single reaction, using Vent polymerase and reaction conditions as suggested by the supplier, containing in addition 2 mM MgSO$_4$, 5% DMSO, and Hot Start Wax beads, with the PCR amplification protocol, as shown below.

| Temperature (° C.) | Time (Min.) | No. Cycles |
|---|---|---|
| 95 | 2 | 1 |
| 95 | 0.5 | |
| 55 | 0.5 | 10 |
| 72 | 0.5 | |

The PCR product is purified using the QIAquick PCR kit, and the purified product then is used in a second PCR amplification, with the primer pair shown below:

AdVA PCR 1F (SEQ ID NO: 31):
5'-ATATATAGAATTCCATGGTCGGGACGC

AdVA PCR 1R (SEQ ID NO: 32):
5'-ATATATGAATTCGCGCAAAAAGCGC

The second PCR amplification of the pol III-based cassette is performed with the Vent polymerase and similar reaction conditions, with the PCR amplification protocol, as shown below.

| Temperature (° C.) | Time (Min.) | No. Cycles |
|---|---|---|
| 95 | 2 | 1 |
| 95 | 0.5 | |
| 55 | 0.5 | 20 |
| 72 | 0.5 | |
| 72 | | 1 |

The products of this second PCR reaction are purified with the QIAquick kit, digested with EcoRI, re-purified and then inserted into the vector pBGSV-gB that also has been digested with EcoRI and treated with alkaline phosphatase. This plasmid is designated pBGSV-gBαBcl.

For a separate set of PCR amplifications, an additional pair of oligonucleotide primers (shown below) is substituted for Ad2Vabcl2F and Ad2Vbcl2R, in order to generate a negative control cassette which allows for construction of the Bcl-2 sequence in the sense orientation.

Ad2VAbcl 3F (SEQ ID NO: 33)
5'AATTCGCAAGGGTATCATGGCGGACGACCGGGGTTCGAACCCCGGAGC

GCACGCTGGGAGAACGGGGTACGACA-3'

Ad2VAbcl 3R (SEQ ID NO: 34)
5'GAATTCGCGCAAAAAGCGCACTATCTCCCGGTTGTCGTACCCCGT-3'

These primers are used as described above to generate a second fragment with EcoRI ends, and that when inserted into pBGSV-gB, results in a plasmid construct designated pBGSV-gBBcl.

Similar constructions that utilize ribozyme sequences (see below) specific for Bcl-2, as well as ribozyme or antisense sequences specific for other anti-apoptotic genes, are readily constructed from these teachings by one of skill in the art.

C. Determination of Immunostimulatory Effects for Proapoptotic Sequences

To demonstrate immunostimulatory effects of these vector modifications, multiple BALB/c mice are immunized intramuscularly with plasmids pBGSV-gB-BAX, pBGSV-gB-BAXrev, pBGSV-gBαBcl, and pBGSV-gBBcl in saline, at doses ranging from 10 ug to 10 ng. Following these immunizations, the level of HSV-gB specific antibody and CTL induced by each construct is determined according to Hariharan et al (ibid). In addition, representative animals also are challenged with virulent HSV to determine the level of protection (Hariharan et al., ibid. Similar levels of immune response or protection at lower DNA doses by the modified vectors compared to the conventional or control vectors is indicative of immune stimulation by the elements of the present invention.

Example 3

Disruption of IRF2 Expression to Enhance Immune Efficacy

In addition to the examples above, the present invention also provides compositions and methods of immune stimulation utilizing specific antisense or ribozyme RNA sequences transcribed in vivo that target one or more mRNAs encoding immune regulatory components. The antisense or ribozyme sequences may co-expressed with a desired antigen from a pathogenic agent, or expressed alone and administered to a warm-blooded animal with or without the desired antigen or antigen-expressing gene delivery vector.

IFNγ plays a major role in the immune response by inducing antiviral and bactericidal activity, stimulating antigen presentation through MHC class I and class II molecules, and by inducing the expression of IFNα and IFNβ genes, as well as a variety of genes whose functions have not yet been determined. A primary response gene to IFNγ is the interferon regulatory factor 1 (IRF1). IRF1 is a transcriptional factor that is expressed at the level of few mRNA copies per cell prior to induction by IFNγ (Fujita et al., *Proc. Natl. Acad. Sci. USA* 86:9936-9940, 1989; Harada et al., *Cell* 58:729-739, 1989). Constitutive expression of IRF1 in transgenic mice results in higher resistance to RNA viruses (Pine, *J. Virol.* 66:4470-4478, 1992) and overexpression in COS cells results in the induction of IFNα and IFNβ without viral stimulation (Fujita et al., *Nature* 337:270-272, 1989). Interferon regulatory factor 2 (IRF2) is a transcriptional inhibitor that is expressed constitutively in many cells and antagonizes IRF1 activity, by binding to the same promoter element in the IFNs and IFN-inducible genes (Harada et al., ibid). Thus, IRF2 is a negative regulator of the IFNγ response.

The present invention provides a mechanism for interfering with IRF2 expression in cells producing an antigen of interest, in order to boost the immune response to that antigen. In particular, a ribozyme or an antisense RNA targeted to IRF2 mRNA is transcribed in vivo from an expression cassette contained within a gene delivery vector, to inhibit IRF2 expression and prolong the IFNγ effects induced by the expression of an antigen of interest. Preferably, the ribozyme or antisense RNA is expressed from the same gene delivery vector encoding the antigen(s) of interest, and is expressed utilizing an RNA polymerase III cassette. In preferred embodiments, the antisense or ribozyme RNA is directed (complementary) to mRNA of the first exon of the IRF2 gene. Since the N-terminal 125 amino acids of IRF2, encoding the transcriptional regulatory activity, exhibit a high degree of homology to the same region in IRF1, exons II, III, and IV are less suitable for targeting.

For example, an RNA polymerase III expression cassette first is constructed to express a hammerhead ribozyme specific for IRF2. A variety of target cleavage sites in the IRF2 mRNA may be chosen and several are depicted in FIG. 6, shown in boldface type. For purposes of this illustration, the chosen target site is boxed and complementary "antisense" sequences used by the ribozyme for target recognition are underlined.

Specifically, the pol III/ribozyme cassette is constructed to contain the following ordered elements: PacI restriction site, Adenovirus 2 VA1 RNA promoter (nucleotides −70/+30), IRF2-specific ribozyme, RNA pol III consensus transcription termination sequence, PacI restriction site. These elements are synthesized using overlapping PCR and cloned into a pUC-derived kanamycin-resistant plasmid DNA vector, pBGSVG (WO 97/38087), with a <PmeI-BglII-XhoI-NotI-EcoRI-PmeI> polylinker sequence and unique PacI site on the opposite side of the vector backbone.

Assembly of the desired components in the pol III-based expression cassette is performed by PCR to juxtapose the following ordered sequences:

```
Ad2 Stuffer (nts. 1051-10584; SEQ ID NO: 35):
5'CCATGGTCGGGACGCTCTGGCCGGTGAGGCGTGCGCAGTCGTTGACGC

TCTGGA-3'
```

```
Ad2 VA1RNA promoter [(-70/+30) (nts.
10585-10682); SEQ ID NO: 36]:
5'CCGTGCAAAAGGAGAGCCTGTAAGCGGGCACTCTTCCGTGGTCTGGTG

GATAAATTCGCAAGGGTATCATGGCGGACGACCGGGGTTCGAACCCCGG

A-3'

IRF2 specific ribozyme (SEQ ID NO: 37)
5'CTCAGTGTGCTTTTTTCACGCCTGATGAGGCCGTGAGGCCGAAACCAA

TACAATTCCGCAAGG-3'

RNA polymerase III termination sequence
(SEQ ID NO: 38):
5'-GCGCTTTTTGCGC-3'
```

Juxtaposition of the sequence elements shown above to construct the pol III-based expression cassette is accomplished in two steps. The first step uses the partially complementary oligonucleotides shown below, each at 1 μM concentration in a short (10 cycle) PCR amplification:

```
VAIRF2-1F (SEQ ID NO: 39):
5'CACACACTTAATTAACCATGGTCGGGACGCTCTGGCCGGTGAGGCGTG

CGCAGTCG-3'

VAIRF2-1R (SEQ ID NO: 40):
5'CCGCTTACAGGCTCTCCTTTTGCACGGTCCAGAGCGTCAACGACTGCG

CACGCCT-3'

VAIRF2-2F (SEQ ID NO: 41):
5'AGAGCCTGTAAGCGGGCACTCTTCCGTGGTCTGGTGGATAAATTCGCA

AGGGTAT-3'

VAIRF2-2R (SEQ ID NO: 42):
5'CACACTGAGTCCGGGGTTCGAACCCCGGTCGTCCGCCATGATACCCTT

GCGAATT-3'

VAIRF2-3F (SEQ ID NO: 43):
5'CCCGGACTCAGTGTGCTTTTTTCACGCCTGATGAGGCCGTGAGGCCGA

AACCAAT-3'

VAIRF2-3R (SEQ ID NO: 44):
5'GTGTGTTTAATTAAGCGCAAAAAGCGCCCTTGCGGAATTGTATTGGTT

TCGGCCTC-3'
```

PCR amplification of the oligonucleotides comprising the pol III-based expression cassette shown above is performed in a single reaction, using Vent polymerase and reaction conditions as suggested by the supplier, containing in addition 2 mM MgSO$_4$, 5% DMSO, and Hot Start Wax beads, with the PCR amplification protocol, as shown below.

| Temperature (° C.) | Time (Min.) | No. Cycles |
|---|---|---|
| 95 | 2 | 1 |
| 95 | 0.5 | |
| 55 | 0.5 | 10 |
| 72 | 0.5 | |

The PCR product is purified using the QIAquick PCR kit, then used in a second PCR amplification, with the VAIRF2-1F and VAIRF2-3R primers. The second PCR amplification of the pol III-based cassette is performed with Vent polymerase and similar reaction conditions, with the PCR amplification protocol shown below.

| Temperature (° C.) | Time (Min.) | No. Cycles |
|---|---|---|
| 95 | 2 | 1 |
| 95 | 0.5 | |
| 55 | 0.5 | 20 |
| 72 | 0.5 | |
| 72 | | 1 |

The product of this second PCR reaction is purified with the QIAquick kit, digested with PacI, re-purified and then inserted into the vector pBGSVG-polII (Example 1) that also has been digested with PacI and treated with alkaline phosphatase. This plasmid-based gene delivery vector is designated pBGSrIRF2.

To demonstrate disruption of IRF2 expression by directed antisense or ribozyme RNAs, a reporter gene system similar to that of Harada et al. (ibid is utilized. In this system, an IRF1/IRF2 binding site is inserted into a reporter construct interposed between an SV40 enhancer element and downstream promoter driving expression of a reporter gene. Transfection of this reporter plasmid into cells expressing IRF2 results in suppression of reporter expression. Co-transfection of the IRF2 expressing cells with the reporter plasmid and a gene delivery vector of the present invention (e.g., pBGSrIRF2 above) allows for a direct measurement of inhibition of IRF2 expression.

Example 4

Disruption of Cyclooxygenase-2 Expression to Inhibit Cancer Cell Growth and Facilitate Host-Mediated Cytotoxicity Against Tumors Prostaglandin E2 (PGE2) is one of several immunosuppressive molecules secreted by tumors and its secretion correlates with tumor progression. The presence of high levels of immunosuppressive molecules is at least partially accountable for a tumor's ability to escape host immune surveillance mechanisms. Cyclooxygenase-2 (COX2) is involved directly in PGE2 synthesis. Several tumors have been found to express high levels of COX2 (Liu et al., *Cancer Res.* 56:5125-5127, 1996; Ristimaki et al., *Cancer Res.* 57:1276-1280, 1997) and its expression correlated with the metastatic potentials (Tsujii et al., *Proc. Natl. Acad. Sci. USA* 94:3336-3340, 1997). The present invention provides gene delivery vectors and methods for targeted disruption (e.g., ribozyme or antisense) of COX2 expression as a mechanism to facilitate antitumor therapy. Since the COX2 cDNA sequence has been established (Hla et al., *Proc. Natl. Acad. Sci. USA* 89:7384-7388, 1992; O'Banion et al., *Proc. Natl. Acad. Sci. USA* 89:4888-4892, 1992), antisense or ribozyme RNAs directed against COX2 mRNA may be designed for insertion into the desired expression cassette, preferably an RNA polymerase III cassette. Other gene products of the PGE2 biosynthetic pathway also may be chosen for targeting according to the present invention. Furthermore, the above described gene delivery vectors also may encode one or more cytokines or tumor antigens.

For example, an RNA polymerase III expression cassette first is constructed to express a hairpin ribozyme specific for COX2. A variety of COX2 mRNA target cleavage sites for hammerhead and hairpin ribozymes may be chosen and are depicted in FIG. 6, shown in boldface type. For purposes of this illustration, the chosen target site is boxed and complementary "antisense" sequences used by the ribozyme for target recognition are underlined.

Specifically, the pol III/ribozyme cassette is constructed to contain the following ordered elements: PacI restriction site, Adenovirus 2 VA1 RNA promoter (nucleotides −70/+30), COX2-specific ribozyme, RNA pol III consensus transcription termination sequence, PacI restriction site. These elements are synthesized using overlapping PCR and cloned into pBGSVG as described in the previous example. Assembly of the desired components in the pol III-based expression cassette is performed by PCR to juxtapose the following ordered sequences:

Ad2 Stuffer (nts. 1051-10584; SEQ ID NO: 45):
5'CCATGGTCGGGACGCTCTGGCCGGTGAGGCGTGCGCAGTCGTTGACGC

TCTGGA-3'

Ad2 VA1RNA promoter [(-70/+30) (nts. 10585-10682;
SEQ ID NO: 46)]:
5'CCGTGCAAAAGGAGAGCCTGTAAGCGGGCACTCTTCCGTGGTCTGGTG

GATAAATTCGCAAGGGTATCATGGCGGACGACCGGGGTTCGAACCCCGG

A-3'

COX2 specific ribozyme (SEQ ID NO: 47)
5'GCAAGGATTTGCTGTATGGCTGAGCGCCAGAGAAGCGCACCAGAGAAA

CACACGTTGTGGTATATTACCTGGTA-3'

RNA polymerase III termination sequence
(SEQ ID NO: 48):
5'-GCGCTTTTTGCGC-3'

Juxtaposition of the sequence elements shown above to construct the pol III-based expression cassette is accomplished in two steps, as described in the previous example, using the following oligonucleotide primers.

VACOX2-1F (SEQ ID NO: 49):
5'CACACATTAATTAACCATGGTCGGGACGCTCTGGCCGGTGAGGCGTGC

GCAGTCGTT

VACOX2-1R (SEQ ID NO: 50):
5'GTGCCCGCTTACAGGCTCTCCTTTTGCTCGGTCCAGAGCGTCAACGAC

TGCGCACGC

VACOX2-2F (SEQ ID NO: 51):
5'CCTGTAAGCGGGCACTCTTCCGTGGTCTGGTGGATAAATTCGCAAGGG

TATCATGGC

VACOX2-2R (SEQ ID NO: 52):
5'ATACAGCAAATCCTTGCTCCGGGGTTCGAACCCCGGTCGTCCGCCATG

ATACCCTTG

VACOX2-3F (SEQ ID NO: 53):
5'AAGGATTTGCTGTATGGCTGAGCGCCAGAGAAGCGCACCAGAGAAACA

CACGTTGTG

VACOX2-3R (SEQ ID NO: 54):
5'TGTGTGTTAATTAAGCGCAAAAAGCGCTACCAGGTAATATACCACAAC

GTGTGTTTC

The PCR product from the first reaction is purified using a QIAquick PCR kit, and then is used in a second PCR amplification with the VACOX2-1F and VACOX2-3R primers. The product of this second PCR reaction is purified with the QIAquick kit, digested with PacI, re-purified and then inserted into the vector pBGSVG-polIII that also has been digested with PacI and treated with alkaline phosphatase. This plasmid is designated pBGSrCOX2.

The ability of gene delivery vectors of the present invention to inhibit COX2 expression may be monitored in cell culture by testing for changes in PGE2 secretion into the culture medium after transfection of the cells with pBGSrCOX2 or the control plasmid pBGSVG. Since colon cancer has been found to produce high levels of PGE2, a cell line derived from this cancer may be particularly suitable for the testing. PGE2 may be detected with commercially available ELISA kits.

Example 5

Suppression of YIN-YANG-1 to Enhance the Immune Response

Several transcription factors are involved in the regulation of IFNγ expression (Young, *J. Interferon & Cyt. Res.* 16:563-568, 1996). Yin-Yang 1 (YY1) is a ubiquitous DNA binding protein that regulates the transcription of several genes, including the oncogenes c-myc and c-fos. According to the context, YY1 can act either as a positive regulator or as a negative regulator. YY1 appears to be involved in the transcriptional repression of IFNγ expression by interacting with multiple sites in the promoter. Mutations in the YY1 binding sites result in an increase of the IFNγ promoter activity (Ye et al., *Mol. Cell. Biol.* 16:4744-4753, 1996). It appears that YY1 represses the IFNγ promoter by binding to a site overlapping with the AP1 binding site, which is required for IFNγ expression (Ye et al., ibid).

Immunization via gene delivery vectors, in particular plasmid DNA, appears to be efficacious in animal models, for inducing antibodies and CD8+ associated CTL responses to the expressed antigen. A desirable feature would be to include some mechanism for the co-induction of CD4+ Th1 associated responses. Since IFNγ plays a major role in these responses, the induction of its expression is required. The present invention utilizes a ribozyme or antisense RNA expressed in vivo, to target YY1 mRNA and down-regulate expression, consequently facilitating the up-regulation of IFNγ expression. The antisense or ribozyme RNA may be expressed utilizing an RNA polymerase III cassette, as well as other RNA polymerase promoters, thus generating a unit that can be cloned into the same gene delivery vector as the antigen of interest. This unit also may be used in conjunction with other mechanisms to boost the immune response, and in particular gene therapy applications for which IFNγ expression is a desirable element.

For example, an RNA polymerase III expression cassette first is constructed to express a hammerhead ribozyme specific for YY1. A variety of YY1 mRNA target cleavage sites for hammerhead and hairpin ribozymes may be chosen and several are depicted in FIG. 6, shown in boldface type. For purposes of this illustration, the chosen target site is boxed and complementary "antisense" sequences used by the ribozyme for target recognition are underlined. Specifically, a pol III-based ribozyme cassette is constructed in pBGSVG, as described in the previous examples. Assembly of the components again is accomplished by overlapping PCR, with the following oligonucleotide primers:

VAYY1-1F (SEQ ID NO: 55):
5'CACACACTTAATTAACCATGGTCGGGACGCTCTGGCCGGTGAGGCGTG

CGCAGTC-3'

-continued

VAIYY1-1R (SEQ ID NO: 56):
5'CGCTTACAGGCTCTCCTTTTGCACGGTCCAGAGCGTCAACGACTGCGC

ACGCCTC-3'

VAIYY1-2F (SEQ ID NO: 57):
5'GAGAGCCTGTAAGCGGGCACTCTTCCGTGGTCTGGTGGATAAATTCGC

AAGGGTA-3'

VAIYY1-2R (SEQ ID NO: 58):
5'CTACATCGTCCGGGGTTCGAACCCCGGTCGTCCGCCATGATACCCTTG

CGAATTT-3'

VAIYY1-3F (SEQ ID NO: 59):
5'CCCCGGACGATGTAGAGGGTGTCGCCCCTGATGAGGCCGTGAGGCCGA

AAGGCCA-3'

VAIRF2-3R (SEQ ID NO: 60):
5'GTGTGTTTAATTAAGCGCAAAAAGCGCGAGCCCTCAGCCATGGCCTTT

CGGCCTC

The PCR product is purified using the QIAquick PCR kit, then used in a second PCR amplification, with the VAIYY1-1F and VAIYY1-3R primers. Next, the product of this second PCR reaction is purified with the QIAquick kit, digested with PacI, re-purified and inserted into pBGSVG-polII that also has been digested with PacI and treated with alkaline phosphatase. This plasmid-based gene delivery vector is designated pBGSrYY1.

Example 6

Disruption of IL10 Expression in Tumor Cells for Anti-Tumor Response

It has been shown that some tumors express and secrete one or more immunosuppressive cytokines. The presence of high levels of these cytokines is at least partially accountable for escape of tumors from host immunosurveillance. IL10 is capable of blocking the activation of several cytokines and several accessory functions of macrophages, T cells, and NK cells (Fortis et al., *Cancer Lett.* 104:1-5, 1996; Gotlieb et al., *Cytokine* 4:385-90, 1992; Nakagomi et al., *Int. J. Cancer* 63:366-71, 1995; Wojciechowska-Lacka et al., *Neoplasma* 43:155-158, 1996). The present invention describes mechanisms whereby the repression of IL10 expression is used in tumors to facilitate host immune clearance of the tumor. This approach may be particularly efficacious when used in combination with immunization to defined tumor antigens.

Specifically, expression cassettes are constructed for the delivery of antisense or ribozyme RNAs that specifically target and prevent expression of IL10. The IL10 cDNA sequence has been determined (Vieira et al., *Proc. Natl. Acad. Sci. USA* 88:1172-1176, 1991), and such RNAs may be delivered and expressed in vivo using any number of different gene delivery vectors, including plasmid DNA. Such vectors may be used alone or in combination with similar cassettes targeted to other immunosuppressive cytokines, and expressed from the same gene delivery vector or from a separate co-administered vector. Furthermore, the vectors of the present invention may be used in conjunction with other genes encoding either cytokines or tumor antigens.

For example, an RNA polymerase III expression cassette first is constructed to express a hairpin ribozyme specific for IL-10. A variety of IL-10 mRNA target cleavage sites for hammerhead and hairpin ribozymes may be chosen and several are depicted in FIG. 6, shown in boldface type. For purposes of this illustration, the chosen target site is boxed and complementary "antisense" sequences used by the ribozyme for target recognition are underlined. Specifically, a pol III-based ribozyme cassette is constructed in pBGSVG, as described in the previous examples. Assembly of the components again is accomplished by overlapping PCR, with the following oligonucleotide primers:

```
VAIL10-1F (SEQ ID NO: 61):
5'CACACATTAATTAACCATGGTCGGGACGCTCTGGCCGGTGAGGCGTGC

GCAGTCGTTG-3'

VAIL10-1R (SEQ ID NO: 62):
5'AGTGCCCGCTTACAGGCTCTCCTTTTGCACGGTCCAGAGCGTCAACGA

CTGCGCACG-3'

VAIL10-2F (SEQ ID NO: 63):
5'CTGTAAGCGGGCACTCTTCCGTGGTCTGGTGGATAAATTCGCAAGGGT

ATCATGGCG-3'

VAIL10-2R (SEQ ID NO: 64):
5'CCCACTTCCCAGGCAACCTCCGGGGTTCGAACCCCGGTCGTCCGCCAT

GATACCCTT-3'

VAIL10-3F (SEQ ID NO: 65):
5'TGCCTGGGAAGTGGGTGCAGCTGTTCTCAAGAAGGGTACCAGAGAAAC

ACACGTTGT-3'

VAIL10-3R (SEQ ID NO: 66):
5'TGTGTGTTAATTAAGCGCAAAAAGCGCTACCAGGTAATATACCACAAC

GTGTGTTTCT-3'
```

The PCR product is purified using the QIAquick PCR kit, then used in a second PCR amplification, with the VAIL10-1F and VAIL10-3R primers. Next, the product of this second PCR reaction is purified with the QIAquick kit, digested with PacI, re-purified and inserted into pBGSVG-polII that also has been digested with PacI and treated with alkaline phosphatase. This plasmid-based gene delivery vector is designated pBGSrIL10.

For each of the previous examples, similar cassettes are readily made by one of skill in the art, wherein the ribozyme sequence is substituted by an alternative ribozyme or an antisense sequence with non-catalytic activity. In such cases, the choice of sequences for targeting may be the same as those described above, or may be specific for other regions of the mRNA molecule.

Example 7

Antigen Co-Expression with Ribozyme/Antisense Cassettes

Antigens derived from a variety of pathogenic agents (e.g., tumor) may be inserted into the RNA polymerase II cassette contained within the above ribozyme or antisense expression plasmids. Alternatively, the antigens may be co-expressed along with the ribozyme or antisense elements in other gene delivery vehicles, such as retroviruses (see for example U.S. Pat. Nos. 5,693,522, 5,691,177, 6,652,130, 5,591,624, and 5,830,458, referenced in their entirety), adenovirus, or AAV.

For example a plasmid DNA vector is constructed that expresses the Her2neu antigen and a ribozyme specific for COX-2. Specifically, the Her2neu antigen is cloned by PCR amplification, using the following oligonucleotide primers incorporate flanking XbaI and NotI restrictions sites.

```
Her2neuFwd (SEQ ID NO: 67)
5'ATATATATCTAGACACCATGGAGCTGGCGGCCTTGT

Her2neuRev (SEQ ID NO: 68)
5'TATATAGCGGCCGCTCACACTGGCACGTCCAGACCCA
```

Following PCR amplification, the product is purified using the QIAquick kit, digested with XbaI and NotI, re-purified with the QIAquick kit, and ligated into plasmid pBGSrCOX2 that also has been digested with XbaI and NotI. The new construct is designated pBGSrCOX2/Her2. Additional constructs that contain modified Her2neu sequences may be generated in a similar manner.

In another example, a plasmid gene delivery vector is constructed that expresses the gp100 antigen and a ribozyme specific for COX-2. Specifically, the gp100 antigen is cloned by PCR amplification, using the following oligonucleotide primers incorporate flanking XbaI and NotI restrictions sites.

```
gp100Fwd (SEQ ID NO: 69)
5'ATATATATCTAGACACAATGGATCTGGTGCTAAAAAGATG gp100Rev (SEQ ID NO: 70)
5'TATATAGCGGCCGCTCAGACCTGCTGCCCACTGAGGAG
```

Following PCR amplification, the product is purified using the QIAquick kit, digested with XbaI and NotI, re-purified with the QIAquick kit, and ligated into plasmid pBGSrCOX2 that also has been digested with XbaI and NotI. The new construct is designated pBGSrCOX2/gp100.

Alternatively, the pol III/ribozyme cassettes and antigen cassettes may be inserted into a variety of other gene delivery vectors (e.g., retrovirus, adenovirus) by one of skill in the art using the teachings of this invention and those references incorporated in their entirety.

Example 8

Animal Models for In Vivo Evaluation of Therapeutic Effectiveness

Several in vivo tumor models may be used for evaluating therapeutic efficacy of these recombinant vectors. For example, using a syngeneic mouse model of melanoma, unmodified B16F10 cells are implanted in C57BL/6 mice at doses of $1 \times 10^5$ cells either subcutaneously to develop a solid tumor nodule, or intravenously to development pulmonary metastases, or both. B16F10 mouse melanoma cells have been demonstrated to express gp100, a melanoma associated tumor antigen. Human melanoma cells have been demonstrated to express gp100 and an antibody response against gp100 is associated with clinical responses. The human and mouse genes for gp100 have been cloned and characterized. Novel gene delivery vectors that express a combination of tumor antigen (e.g., gp100) and antisense/ribozyme RNA (e.g., antisense specific for COX2, TGF-β) may be evaluated for in vivo efficacy as generally described by Karavodin et al. (*Human Gene Therapy* 9:2231-2241, 1998). Specifically, such vectors are evaluated for therapeutic activity in vivo by implanting subcutaneously (s.c.) $1 \times 10^5$ B16F10 melanoma cells into the lower ventral abdomen of 6-8 week old female mice. A palpable tumor nodule is allowed to form at the site of injection for 7-10 days or until the nodule is 2-5 mm in diameter. Measurement and recording of tumor diameter or volume of the s.c. tumor before, during and after treatment is used to indicate therapeutic effectiveness. Sacrifice of the animal and removal of the lungs to visually enumerate tumor cell foci is used as a measurement of systemic anti-tumor response. Alternatively, serum anti-tumor antibodies or in vitro bulk cytolytic T cell (CTL) activity may be assayed using standard immunological approaches to determine systemic therapeutic responses. The therapeutic vector may be injected intratumorally, peritumorally, or a combination of both in volumes such as 50-100 µL. Treatment schedules may be one or two injections per day given over 5 to 7 consecutive days of vector that is $1\times10^8$ cfu/ml or 1-100 ug or greater.

Alternatively, evaluation of a gene delivery vector expressing the Her2/neu tumor antigen and an antisense/ribozyme inhibitor (e.g., specific for COX-2) may be performed in a Her2/neu transgenic mouse model as described by Boggio et al., (*J. Exp. Med.* 188:589-596, 1998). Briefly, transgenic mice develop spontaneous mammary tumors that will involve all mammary glands by about 33 months of age. In a vaccination application, mice are given injections of the therapeutic vector intramuscularly or subcutaneously prior to the development of palpable tumors. Various vaccination schedules are used (e.g., once a week for 4-6 weeks, or once a month for 3-4 months), with 50-100 µL of viral vector at titers of $1\text{-}100\times10^6$ cfu/ml or 1-100 ug of a DNA vector. These vectors also may be used in a therapeutic application wherein mice with existing tumors are injected. The therapeutic vector is injected intratumorally, peritumorally, or a combination of both, in volumes of 50-100 µL. Various treatment schedules are utilized, for example, including one or two injections per day given over 5 to 7 consecutive days of vector that is $1\times10^8$ cfu/ml or greater.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A method of stimulating an immune response to a selected antigen within a desired host, comprising administering to the host a gene delivery vector comprising an expression cassette, wherein the expression cassette comprises:
   a promoter operably linked to a first nucleic acid molecule that encodes a ribonucleic acid (RNA) which comprises a sense RNA encoded by SEQ ID NO:7, which, when transcribed in vivo, forms double stranded RNA via self-complementing sequences within the RNA, wherein the double stranded RNA induces the production of interferon; and
   an RNA polymerase II promoter operably linked to a second nucleic acid molecule that encodes an antigen from a pathogenic agent or a tumor.

2. The method of claim 1 wherein the pathogenic agent is a viral agent.

3. The method of claim 2 wherein the viral agent is selected from the group consisting of HIV, HSV, HBV, HCV, HPV, and FIV.

4. The method of claim 1 wherein the pathogenic agent is a bacterium, parasite, or fungus.

5. The method of claim 1 wherein the antigen is from a tumor.

6. The method of claim 1 wherein the RNA polymerase II promoter is selected from the group consisting of CMV, SV40, MoMLV LTR, and RSV LTR.

7. The method of claim 1 wherein the gene delivery vector is a plasmid.

8. The method of claim 1 wherein the gene delivery vector is a recombinant retrovirus.

9. The method of claim 1 wherein the gene delivery vector is a recombinant herpes virus.

10. The method of claim 1 wherein the gene delivery vector is a recombinant poxvirus.

11. The method of claim 1 wherein the gene delivery vector is a recombinant adenovirus.

12. The method of claim 1 wherein the gene delivery vector is a recombinant parvovirus.

13. The method of claim 1 wherein the gene delivery vector is a recombinant alphavirus.

14. The method of claim 1 wherein the gene delivery vector is a recombinant polyoma virus.

15. The method of claim 1 wherein the gene delivery vector is a eukaryotic layered vector initiation system.

* * * * *